United States Patent [19]

Herr et al.

[11] Patent Number: 5,436,157
[45] Date of Patent: Jul. 25, 1995

[54] HUMAN INTRA-ACROSOMAL SPERM ANTIGEN

[75] Inventors: John C. Herr, Charlottesville; Richard M. Wright, Palmyra, both of Va.

[73] Assignee: The University of Virginia Alumni Patents Foundation, Charlottesville, Va.

[21] Appl. No.: 481,491

[22] Filed: Feb. 16, 1990

Related U.S. Application Data

[63] Continuation-in-part of Ser. No. 318,551, Mar. 3, 1989, abandoned.

[51] Int. Cl.[6] ................. C12N 15/12; C12N 15/70
[52] U.S. Cl. ..................... 435/252.33; 435/69.1; 435/69.3; 435/252.3; 435/320.1; 536/23.5; 530/852; 424/185.1; 424/811
[58] Field of Search ........... 435/69.3, 240, 26, 252.33, 435/172.3, 172.1, 172.2, 69.1, 320.1, 252.3; 424/88, 185.1; 514/21; 530/852; 536/27, 23.5

[56] References Cited

U.S. PATENT DOCUMENTS

| | | | |
|---|---|---|---|
| 4,741,998 | 5/1988 | Herr et al. | 435/7 |
| 4,782,136 | 11/1988 | Goldberg et al. | 530/326 |
| 5,047,508 | 9/1991 | Herr et al. | 530/387 |

FOREIGN PATENT DOCUMENTS 0204566 12/1986 European Pat. Off. ...... A61K 39/00

OTHER PUBLICATIONS

Akekunle et al (1989) Biol. Reprod., 40:127–134.
Doege et al (1987) JBC 262(36):17757–17767.
Millan et al. (1987) PNAS USA 84:5311–5315.
Young et al (1983) PNAS USA 80:1194–1196.
Yi et al (1991) Biol. Reprod. 44:332–337.
Cowan et al (1986) J. Cell Biol. 103:1289–1297.
Hardy et al (1988) Biology of Reproduction 38:423–437.
Herr et al (1990) Biology of Reproduction 42:181–193.
Lee et al (1986) J. Reprod. Immunol. 9:261–274.
Liu et al (1989) Int. J. Andrology 12:451–463.
Anderson et al., *Journal of Reproductive Immunology*, 10:231–257 (1987).
Herr et al., *J. Andrology*, 9:42 (1988), 13th Ann. Meet. Abst. #96.
Kallajoki et al., *International Journal of Andrology*, 7:283–296 (1984).
Kallajoki et al., *International Journal of Andrology*, 9:181–194 (1986).
Salonen et al., *International Journal of Andrology*, 10:731–739 (1987).
Kallajoki et al., *Biology of Reproduction*, 35:157–165 (1986).
Lee et al., *J. Reproductive Immunology*, 4:173–181 (1982).
Huneau et al., *International Journal of Andrology*, 11:13–24 (1987).
Primakoff et al., *Nature*, 335:543–546 (1988).
Herr et al., *Journal of Forensic Sciences*, 32:346–356 (1987).
Herr et al., *Biology of Reproduction*, 35:773–784 (1986).
Maruyama et al., *Journal of Andrology*, 6:127–135 (1985).

(List continued on next page.)

*Primary Examiner*—Kay K. A. Kim
*Attorney, Agent, or Firm*—Oblon, Spivak, McClelland, Maier & Neustadt

[57] ABSTRACT

A substantially purified intra-acrosomal human sperm antigen useful in a contraceptive vaccine is disclosed herein. The antigen remains associated with human sperm after the acrosome reaction. In particular, it remains associated with the inner and outer acrosomal membranes. Modified antigens and fragments thereof prepared by protein modification techniques are also disclosed as well as methods for purifying and using the antigens. Also disclosed are monoclonal and polyclonal antibodies to the antigen and methods of making and using such antibodies. Methods of use include purification of the antigen or use in various diagnostic techniques. Also disclosed are cDNA, expression vectors, and transformed microorganisms that produce the antigen.

4 Claims, 17 Drawing Sheets

OTHER PUBLICATIONS

Wolff et al., *Fertility and Sterility*, 49:497–504 (1988).
Marx, *Science*, 240:1616–1618 (1988).
Moss, *ABA Journal*, pp. 66–70 (May 1988).
Gaensslen, "Identification of Semen and Vaginal Secretions," *Sourcebook in Forensic Serology, Immunology, and Biochemistry*, 149–181 (1983).
Comhaire et al., "The Significance of Semen Analysis for the Evaluation of Male Fertility," in *Male Fertility: Diagnosis and Management*, pp. 34–47 (Date Unknown).
Wolf et al., *Biology of Reproduction*, 29:713–723 (1983).
Isojima et al., *Journal of Reproductive Immunology*, 10:67–78 (1987).
Yan et al., *American Journal of Reproductive Immunology*, 4:111–115 (1983).
Paul et al., *Clinical Reproduction and Fertility*, 1:235–240 (1982).
Hancock et al., *Journal of Reproductive Immunology*, 7:215–223 (1985).
Kyurkchiev et al., *Immunology*, 57:489–492 (1986).
Isojima et al., *Clin. Exp. Immunol.*, 49:449–456 (1982).
Isojima et al., *Immunological Approaches to Contraception and Promotion of Fertility*, (Talwar Ed.), 323–333 (Plenum Publishing, 1986).
Chang et al., *Science*, 240:324–326 (1988).
Anderson et al., *Fertility and Sterility*, 40:557–571 (1983).
Naz, *Journal of Reproductive Immunology*, 11:117–133 (1987).
Yanagimachi, "Mammalian Fertilization," in *The Physiology of Reproduction*, (Knobil et al. Eds.), pp. 135–185 (Raven Press 1988).
Nagae et al., *Fertility and Sterlity*, 45:701–707 (1986).
Yudin et al., *Gamete Research*, 20:11–24 (1988).
Cross et al., *Gamete Research*, 15:213–226 (1986).
Abstract No. 225934, Anderson et al., *Journal of Reproductive Immunology*, 10:231–257 (1987).
*Biological Abstracts*, vol. 79(5) Abstract No. 44868, Kallajoki et al., *International Journal of Andrology*, 7:283–296 (1984).
Gould et al., *Developmental Biology*, 117:306–318 (1986).
*Biological Abstracts*, vol. 89, Abstract No. 120800, Herr et al., *Biol. Reprod*, 42:181–194 (1990).
*Biological Abstracts*, vol. 86(7), Abstract No. 75251, Yudin et al., *Gamete Res.*, 20:11–24 (1988).
*Biological Abstracts*, vol. 84(12), Abstract No. 124183, Mortimer et al., *Reprod. Fertil.*, 81:127–136 (1987).
Biological Abstracts, vol. 77(5), Abstract No. 39354, Working et al., J. Exp. Zool., 227:97–108 (1983).
Noland et al., *J. Biological Chemistry*, 264:13586–13590 (1989).
Sofer et al., *BioTechniques*, pp. 198–203 (Nov./Dec. 1983).
PCT Search Report dated Jul. 26, 1990.
Wright et al., *Biol. Reproduction*, 42:693–701 (1990).
Baba et al., *FEBS Letters*, 244:296–300 (1989).

```
5'
                    GGTTTCTCTTGCTAATGAGTCTT
AATTCGGGGCTATGAAGCAGCTGTGGCCCACACTGGGGTCCCCTC
           TER
TTTTCCTAAATCCAGATGAACAGGTTTCTCTTGCTAATGAGTCTT         90
    TER       M  N  R  F  L  L  L  M  S  L           10

TATCTGCTTGGATCTGCCAGAGGAACATCAAGTCAGCCTAATGAG
TATCTGCTTGGATCTGCCAGAGGAACATCAAGTCAGCCTAATGAG
  Y  L  L  G  S  A  R  G  T  S  S  Q  P  N  E

CTTTCTGGCTCCATAGATCATCAAACTTCAGTTCAGCAACTTCCA         180
CTTTCTGGCTCCATAGATCATCAAACTTCAGTTCAGCAACTTCCA
  L  S  G  S  I  D  H  Q  T  S  V  Q  Q  L  P       40

GGTGAGTTCTTTTCACTTGAAAACCCTTCTGATGCTGAGGCTTTA
GGTGAGTTCTTTTCACTTGAAAACCCTTCTGATGCTGAGGCTTTA
  G  E  F  F  S  L  E  N  P  S  D  A  E  A  L
                        -cho- TATGAGACTTCTTCAGGCCTGAACACTTTAAGTGAGCATGGTTCC         270
TATGAGACTTCTTCAGGCCTGAACACTTTAAGTGAGCATGGTTCC
  Y  E  T  S  S  G  L  N  T  L  S  E  H  G  S       70

AGTGAGCATGGTTCAAGCAAGCACACTGTGGCCGAGCACACTTCT
AGTGAGCATGGTTCAAGCAAGCACACTGTGGCCGAGCACACTTCT
  S  E  H  G  S  S  K  H  T  V  A  E  H  T  S

GGAGAACATGCTGAGAGTGAGCATGCTTCAGGTGAGCCCGCTGCG         360
GGAGAACATGCTGAGAGTGAGCATGCTTCAGGTGAGCCCGCTGCG
  G  E  H  A  E  S  E  H  A  S  G  E  P  A  A     100

ACTGAACATGCTGAAGGTGAGCATACTGTAGGTGAGCAGCCTTCA
ACTGAACATGCTGAAGGTGAGCATACTGTAGGTGAGCAGCCTTCA
  T  E  H  A  E  G  E  H  T  V  G  E  Q  P  S

GGAGAACAGCCTTCAGGTGAACACCTCTCCGGAGAACAGCCTTTG         450
GGAGAACAGCCTTCAGGTGAACACCTCTCCGGAGAACAGCCTTTG
  G  E  Q  P  S  G  E  H  L  S  G  E  Q  P  L     130

AGTGAGCTTGAGTCAGGTGAACAGCCTTCAGATGAACAGCCTTCA
AGTGAGCTTGAGTCAGGTGAACAGCCTTCAGATGAACAGCCTTCA
  S  E  L  E  S  G  E  Q  P  S  D  E  Q  P  S
                              +  +  +  +

GGTGAACATGGCTCCGGTGAACAGCCTTCTGGTGAGCAGGCCTCG         540
GGTGAACATGGCTCCGGTGAACAGCCTTCTGGTGAGCAGGCCTCG
  G  E  H  G  S  G  E  Q  P  S  G  E  Q  A  S     160
```

FIG.11A

```
                                            5'
GGTGAACAGCCTTCAGGTGAGCACGCTTCAGGGGAACAGGCTTCA
GGTGAACAGCCTT————————————————————————————————
  G  E  Q  P  S  G  E  H  A  S  G  E  Q  A  S
               ===========    ============

GGTGCACCAATTTCAAGCACATCTACAGGCACAATATTAAATTGC      630
——————————————————————————CAGGCACAATATTAAATTGC
  G  A  P  I  S  S  T  S  T  G  T  I  L  N  C     190
              +  +  +  +  +

TACACATGTGCTTATATGAATGATCAAGGAAAATGTCTTCGTGGA
TACACATGTGCTTATATGAATGATCAAGGAAAATGTCTTCGTGGA
  Y  T  C  A  Y  M  N  D  Q  G  K  C  L  R  G

GAGGGAACCTGCATCACTCAGAATTCCCAGCAGTGCATGTTAAAG      720
GAGGGAACCTGCATCACTCAGAATTCCCAGCAGTGCATGTTAAAG
  E  G  T  C  I  T  Q  N  S  Q  Q  C  M  L  K     220

AAGATCTTTGAAGGTGGAAAAACTCCAATTCATGGTTCAAGGGTGT
AAGATCTTTGAAGGTGGAAAAACTCCAATTCATGGTTCAAGGGTGT
  K  I  F  E  G  G  K  L  Q  F  M  V  Q  G  C

GAGAACATGTGCCCATCTATGAACCTCTTCTCCCATGGAACGAGG      810
GAGAACATGTGCCCATCTATGAACCTCTTCTCCCATGGAACGAGG
  E  N  M  C  P  S  M  N  L  F  S  H  G  T  R     250

ATGCAAATTATATGCTGTCGAAATCAATCTTTCTGCAATAAGATC
ATGCAAATTATATGCTGTCGAAATCAATCTTTCTGCAATAAGATC
  M  Q  I  I  C  C  R  N  Q  S  F  C  N  K  I
                       -cho- TAGAAGCCTGGGCCCTTGCTTGTTTTGACTCAGGCAGTAAAAAGC      900
TAGAAGCCTGGGCCCTTGCTTGTTTTGACTCAGGCAGTAAAAAGC
 TER                                               265

CTCCATCACTCTATTTGGCTCATTTTATATTTAGTTCCTTCCCCA
CTCCATCACTCTATTTGGCTCATTTTATATTTAGTTCCTTCCCCA
                                 *****

GTCAACAACTGACCACATCTGCCTCTGCCTGAGCATTAGGATGCT      990
GTCAACAACTGACCACATCTGCCTCTGCCTGAGCATTAGGATGCT

CAAACATCCTATCTTTCTTCTTCTATTCATGCTTTTATCCATTCT
CAAACATCCTATCTTTCTTCTTCTATTCATGCTTTTATCCATTCT

TCTCTGTCCTGTCTTCCCTGCTCCAACTCTTTCTCTCAATATTCC      1080
TCTCTGTCCTGTCTTCCCTGCTCCAACTCTTTCTCTCAATATTCC

TGATTTTTTTTTCAATAAATTTCACATGCCCGAATTC      3'
TGATTTTTTTTT ^^^^^^                                1117
```

FIG. 11B

FIG. 13A
FIG. 13B
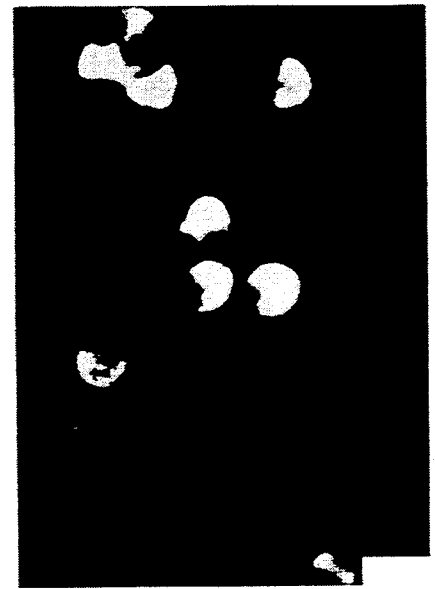
FIG. 13C
FIG. 13D

HUMAN INTRA-ACROSOMAL SPERM ANTIGEN The United States Government has certain rights in the invention described and claimed herein as a result of its support of certain work related to the invention under grants from the National Institutes of Health.

BACKGROUND OF THE INVENTION

This application is a continuation-in-part of application Ser. No. 318,551 filed Mar. 3, 1989 now abandoned and incorporated herein by reference.

This invention relates to contraceptive vaccines. In particular, it relates to a class of intra-acrosomal human sperm antigens for use in a contraceptive vaccine, a class of monoclonal and polyclonal antibodies to the antigens, and related methods of making and using the antigens and antibodies, including a cDNA expression system for the production of the antigen in vitro.

Antibodies to sperm have been implicated in human infertility, and the deliberate immunization of animals with sperm or mature testis extracts has resulted in a significant inhibition of fertility. Accordingly, researchers have actively pursued the study of sperm antigens in the hopes of identifying a germ cell specific antigen that can be used as an immunogen in a contraceptive vaccine. The approach of identifying gamete specific antigens has the advantage over other approaches, such as the HCG vaccine, of being a pre-fertilization vaccine—one which induces immunity which blocks fertilization as opposed to attacking the early embryo.

A safe and effective contraceptive vaccine would be a highly desirable method of birth control because a single injection or only a very few injections could provide antifertility activity in a human female for several years. However, until relatively recent biotechnologic and immunologic advances, very few antigens suitable for such antifertility vaccines had been identified and purified, especially in humans. Further, human proteins were significantly more difficult and expensive to produce than most viral or bacterial proteins, and were not as immunogenic. The emergence of hybridoma and recombinant DNA technology has provided the possibility of identifying germ cell specific antigens and mass producing the human form of such protein antigens for study and potential use in new vaccines.

Anderson and Alexander, *Fertility and Sterility*, 40:557–571 (1983) discusses the general application of genetic engineering and monoclonal antibody technology to developing antifertility vaccines. It also discusses some of the candidates for such vaccines, including the sperm antigens protamine, lactate dehydrogenase-$C_4$ (LDH-$C_4$), RSA-1, acrosin, and hyaluronidase. The authors state that LDH-$C_4$ has been purified and amino acid sequence information is available. They further state that monoclonal antibodies (MABs) have been developed to it. The authors also state on page 561 that (1) sperm plasma membrane autoantigens provide the best targets for the effects of antifertility antibodies and (2) antigens bound to the inner acrosomal membrane, such as acrosin and hyaluronidase, appear to be poor candidates.

Over the last several years, many different monoclonal antibodies have been made to human and other animal sperm antigens. For example, Lee et al., *Journal of Reproductive Immunology*, 4:173–181 (1982), incorporated herein by reference, discloses mouse MABs that react with antigens localized in the acrosomal region of human sperm. Such antigens are apparently on the surface of the sperm, and they have a molecular weight of about 10,000.

Another example is a mouse MAB, designated C11H, to an acrosomal antigen. See Kallajoki and Souminen, *International Journal of Andrology*, 7:283–296 (1984), Kallajoki et al., *International Journal of Andrology*, 9:181–194 (1986), and Salonen and Kallajoki, *International Journal of Andrology*, 10:731–739 (1987), all of which are incorporated herein by reference. The 1984 paper discloses the preparation of C11H and that it recognized an antigen of 50,000 molecular weight as well as other components of 24,000–34,000 molecular weight. The antigen was found in the sperm of humans and certain animals. The authors indicated that they believed the antigen to be acrosin, and they stated that they did not know whether it was in the acrosome or within the acrosomal membranes. The 1986 paper provides further information about the antibody and antigen. The authors state that the antibody reacted with acrosin and further that acrosin is in the acrosomal matrix. They suggested that acrosin is almost totally liberated during the acrosome reaction. They further state that it reacted against a 50 Kd antigen and several others in the 24–34 Kd range. Finally, they state that the MAB can be used to screen for acrosome-reacted sperm. The 1987 paper discloses experiments in which C11H inhibited sperm penetration of zona-free hamster eggs.

Huneau et al., *International Journal of Andrology* 11:13–24 (1987), incorporated herein by reference, discloses a mouse MAB, designated a-HS 1E.1, which reacts with human sperm in the equitorial region of the acrosomal membrane. FIG. 2 in the paper indicates that the MAB reacts with the outer acrosomal membrane. The corresponding antigen has a molecular weight equal to or greater than 53 Kd.

Such antibodies provided the possibility, at least in theory, of identifying, isolating, and characterizing gamete cell specific antigens that might be useful in a contraceptive vaccine. However, the efforts to date have been disappointing.

Anderson et al., *Journal of Reproductive Immunology*, 10:231–257 (1987), incorporated herein by reference, discloses a multi-laboratory effort sponsored by the World Health Organization (WHO) to evaluate 66 different mouse MABs that react with human sperm. Of the 66, only 3 reacted with antigens that looked like good candidates for a contraceptive vaccine. One of these monoclonal antibodies, designated MHS-10, showed strong human sperm and testicular germ cell reactivity and a lack of cross-reactivity with many other adult tissues. The antibody inhibited fertilization in the hamster egg penetration test. The authors also stated that MHS-10 bound to a human sperm surface antigen and that it reacted with a family of antigens with molecular weight between 14,000 and 30,000.

The authors disclosed various difficulties in evaluating this MAB and the other MABs. They concluded from their evaluation of all of the antibodies that the mouse monoclonal antibody approach is not efficient for the identification of human reproductive tissue-specific antigens and further that the immunohistological data and the "surprising cross-reactivity of the MABs with non-reproductive tissues" underline the necessity for extensive immunohistologic testing of new MABs by qualified immunopathology groups.

At least one recent study continues to reflect the conventional wisdom that an antifertility antigen should appear on the sperm surface. Primakoff et al., *Nature*, 355:543–546 (1988), incorporated herein by reference, reports an affinity-purified guinea pig sperm protein, designated PH-20, which was used as an immunogen to prevent conception in male and female guinea pigs. The antigen, which has a molecular weight of 64,000, is present on both the plasma membrane and inner acrosomal membrane of guinea pig sperm. In the last paragraph of the article, the authors state that the high contraceptive effectiveness of the antigen depends upon several specific properties, including its presence on the sperm surface. They further state that a human functional analog of PH-20 would be a candidate for an effective contraceptive immunogen.

Herr et al., *Journal of Andrology*, 9:42 (1988) is an abstract that reports further data on the antigen identified by MHS-10. In particular, it discloses that the antigen is localized to acrosome-shaped structures in the human sperm and that the peptide has 7 major isoforms with a molecular weight of 22–38 kD.

MSH-10 and its corresponding antigen, human acrosomal sperm antigen 10 (SP-10), have now been substantially purified and characterized by the inventors. The inventors have surprisingly discovered a class of intra-acrosomal human sperm antigens that, contrary to the conventional wisdom, may have antifertility activity when used as an immunogen in a contraceptive vaccine for human females. The inventors have also isolated the cDNA coding for the SP-10 antigen, which permits the use of genetic engineering methods for making the antigens in a form useful as a immunogen in a vaccine.

SUMMARY OF THE INVENTION

It is an object of the invention to provide a substantially purified intra-acrosomal human sperm antigen for use in a contraceptive vaccine. Another object of the invention is to provide a composition for use as a contraceptive vaccine.

A further object of the invention is to provide a method for producing the antigen.

It is a further object of the invention to provide monoclonal and polyclonal antibodies that reacts with the intra-acrosomal human sperm antigen of the invention and methods for producing the antibodies.

Still another object of the invention is to provide a composition and method for detecting human sperm or isolating such sperm.

Still another object is to provide methods and compositions for the biochemical, immunological, functional, or other investigational analysis of human sperm.

Still another object of the invention is to provide a method for detecting immature germ cells in semen and the application of this method in assessing infertility.

Still another object is to provide a DNA sequence and expression vector that code for the antigen of the invention.

A further object of the present invention is the identification of immunogenic peptides of the antigen.

Yet another object of the invention is to provide transformed microorganisms that produce the antigen.

Additional objects and advantages of the invention will be set forth in part in the description which follows, and in part will be obvious from the description, or may be learned by practice of the invention. The objects and advantages of the invention will be attained by means of the instrumentalities and combinations particularly pointed out in the appended claims.

To achieve the objects and in accordance with the purpose of the invention, as embodied and broadly described herein, a substantially purified intra-acrosomal human sperm antigen that remains associated with the sperm after the acrosome reaction is disclosed herein. Preferably, following the acrosome reaction, the antigen remains associated with the sperm head, and most preferably it is associated with either the outer aspect of the inner acrosomal membrane or with the equatorial segment of the sperm.

An alternative embodiment of the invention is a substantially pure polypeptide that exhibits substantial homology to this antigen or has been altered to provide a polypeptide having enhanced antifertility immunogenicity when compared to the unaltered polypeptide.

Also described herein is a method for producing the native antigen of the invention. Mature human sperm are homogenized, and soluble proteins are extracted. The extract is contacted with an immobilized monoclonal antibody that reacts with the antigen of the invention to form an immobilized complex of the antibody and the antigen. The antigen is then separated from monoclonal antibody to be recovered in substantially purified form.

Also described herein is an alternative method for producing the native antigen from human sperm. Ejaculated sperm are homogenized and the soluble proteins are separated by reverse phase high pressure liquid chromatography. SP-10 peptides are then further purified by preparative SDS-PAGE.

The invention also provides a monoclonal antibody to the intra-acrosomal human sperm antigen. The antibody lacks cross-reactivity with a substantially all human somatic tissues and inhibits sperm-egg interactions in the hamster egg penetration test.

The monoclonal antibody is produced by immunizing a mammal with acrosome-reacted human sperm or the supernatant obtained from centrifuging acrosome-reacted human sperm. The antibody-producing cells from the mammal are obtained and fused with tumor cells to produce hybridomas. The hybridomas are screened with acrosome-reacted human sperm or the supernatant obtained from centrifuging such sperm in order to identify hybridomas that produce the antibody reactive with the intra-acrosomal human sperm antigen. The antibody is then recovered from the identified hybridomas.

In addition to purifying the antigen of the invention, the monoclonal antibodies disclosed herein are useful for detecting or isolating human sperm that have undergone the acrosome reaction. The antibody is contacted with a sample of human sperm for a time and under conditions sufficient for the antibody and any acrosome-reacted sperm to form an antigen-antibody complex. The complexes are then detected or removed from the sample. In the latter case, the sperm cells are then separated from the complex and recovered as an isolate.

In an alternative and preferred embodiment, the antigen of the invention is produced by culturing host cells transformed by an expression vector that directs the expression of the antigen in the transformed microorganism. The expression vector comprises a recombinant DNA sequence containing a cDNA sequence that codes for the antigen operably linked to appropriate regulatory control nucleic acid sequences.

The accompanying figures, which are incorporated in and constitute a part of the specification, illustrate an embodiment of the invention and, together with the description, serve to explain the principles of the invention.

BRIEF DESCRIPTION OF THE DRAWINGS

FIG. 1. Immunohistochemical localization of SP-10 within seminiferous tubules of the human testis.

FIG. 2. Immunofluorescent light micrographs localizing SP-10 in ejaculated human sperm.

FIG. 11. FIG. 11A and FIG. 11B. Complete nucleotide and predicted protein sequences derived from overlapping SP-10-5 and SP-10-10 cDNAs. The single letter amino acid code for the protein sequence is indicated below the nucleotide sequence. The top line in each pair of sequences was derived from the SP-10-5 cDNA and the bottom line from the SP-10-10 cDNA as indicated. The numbering to the right indicates the nucleotide and amino acid positions. The solid line in the SP-10-10 sequence spanning nucleotides 554–610 represents the putative alternatively spliced region of SP-10-10. Repeated motifs one, two, and three are designated by single, double, and triple underlined sequences respectively. Sites of potential N-linked glycosylation are denoted by the symbol -cho-, and sites of potential O-linked glycosylation are underscored with the symbol (+++). The 5' consensus nucleotide sequence flanking eukaryotic ATG start codons is underscored with the symbol (~~~), a poly A addition signal is underscored with the symbol (···), and a mRNA consensus degradation sequence is underscored with the symbol (***). The two in-frame termination codons 5' of the ATG are designated by TER. An internal EcoR1 site is indicated at the arrowhead.

FIG. 13. Immunofluorescent staining of human sperm using MHS-10 and the SP-10 polyclonal antisera. Both the MHS-10 monoclonal antibody and the polyclonal antiserum to recombinant fusion protein pWRSP-210 react with the acrosomal cap. Sperm incubated with SP-10 polyclonal antiserum, x1200 (A), preimmune sera, x1200 (B), MHS-10 monoclonal, x1775 (C), or null ascities, x1775 (D).

FIG. 14.

FIG. 15I. Pleomorphic fragments of sperm heads in semen showing immunohistostaining material (MHS-10, SBP, hematoxylin x2149).

DESCRIPTION OF THE PREFERRED EMBODIMENTS

Figure 1A:
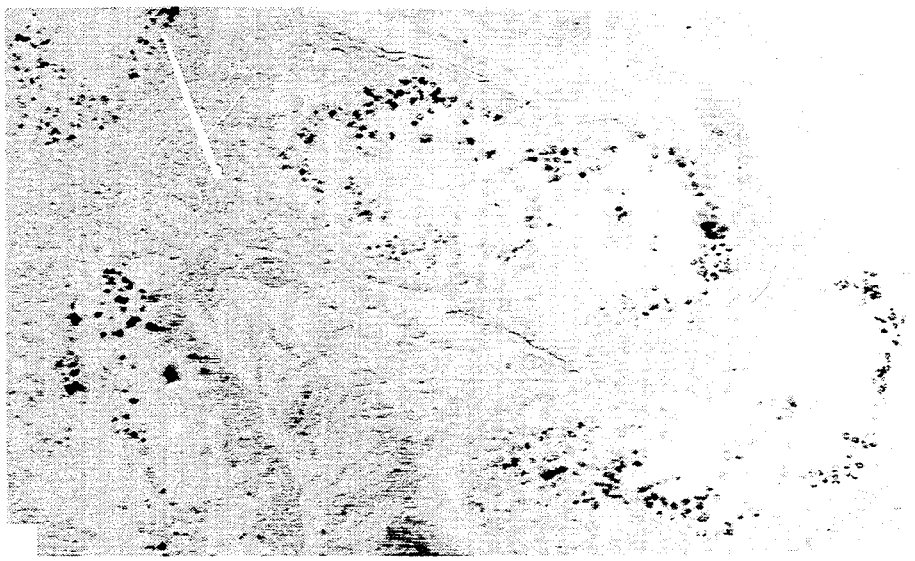
FIG. 1A. Cross sections of seminiferous tubules reacted with the MHS-10 monoclonal antibody (1:1000) demonstrate dark reaction product in the adluminal compartment. X 180.

Reference will now be made in detail to the presently preferred embodiments of the invention, which, together with the following examples, serve to explain the principles of the invention.

The invention relates to an intra-acrosomal human sperm antigen that remains associated with human sperm after the acrosome reaction. Prior to the acrosome reaction, the antigen is observed within the acrosome. It is possible that the antigen is soluble in the acrosome matrix prior to the acrosome reaction. After the acrosome reaction, it remains displayed on the sperm head. In a preferred embodiment, the antigen is associated in intact, non-acrosome-reacted sperm with the outer aspect of the inner acrosomal membrane and the inner aspect of the outer acrosomal membrane, and it remains associated with those membranes after the acrosome reaction. Most preferably, the antigen is retained in association with the inner acrosomal membranes and the equatorial segment in acrosome-reacted human sperm. As used herein, the term "associated with" or variations thereof means bound with a hydrophobic tail inserted into the membrane or loosely bound by electrostatic interactions and includes being unbound in the acrosome matrix prior to the acrosome reaction.

The antigen of the invention is testis specific and conserved in the human population. It appears to be a differentiation antigen that arises during spermatogenesis. It appears to be located in the acrosomal matrix of immature human sperm prior to the acrosome reaction.

Preferably, the antigen is substantially purified. The terms "substantially pure" and "substantially purified" and variations thereof, when used to refer to the antigen disclosed herein, shall mean the antigen substantially free of proteins or polypeptides that are not the intra-acrosomal human sperm antigen. In the context of the preferred antigen, substantially pure means that, when the purified antigen is sequenced by amino terminal amino acid sequencing, the resultant sequence compares with the deduced amino acid sequence obtained from the open reading frame of the cDNAs. The substantially pure antigen of the present invention is at least 90% pure by weight, preferably at least 95% pure by weight, and most preferably at least 98% pure by weight. That is, the substantially pure antigen of the invention contains no more than 10%, preferably no more than 5%, and most preferably no more than 2% by weight of proteins or polypeptides that are not the antigen. The purity was determined by densitometric scanning of SDS-PAGE gels stained with Amindo Black which contained the purified SP-10 antigen and by amino acid sequencing the $NH_2$ terminus of the purified protein.

In a particularly preferred embodiment, the antigen is substantially purified and comprises a family of proteins or polypeptides having a molecular weight from about 18 to about 34 kilodaltons as determined by sodium dodesylsulfate (SDS) polyacrylamide gel electrophoresis. Immunoreactive peptides with molecular weights from 24–34 kDa had an isoelectric point of approximately 4.9, while immunoreactive peptides in the 18 kDa range had pIs of 5.1–5.4, as determined by isoelectric focusing. The immunoreactive peptides appear to be single-chained, since a reduction of the disulfide bonds did not alter the apparent molecular weights. In a particularly preferred embodiment, the antigen reacts with monoclonal antibodies produced by the cell line designated ATCC HB 10039 or mutants or variants thereof.

The antigen of the invention is obtained in substantially purified form by known protein extraction techniques that have been modified in accordance with the discoveries and teachings described herein. Mature human sperm are collected and homogenized. The soluble proteins, including the antigen, are extracted from the homogenate by known protein extraction techniques. The extract is then brought into contact with a monoclonal antibody reactive with the antigen. The antibody and antigen react to form a complex. Generally, the monoclonal antibody is immobilized, such as by conjugation to a solid substrate, so that the antigen may be removed from the extract. Preferably, the solid substrate, which contains the antibody-antigen complex, is then washed to remove other proteins and contaminants. The antigen is then separated from the monoclonal antibody by known techniques and recovered in substantially purified form. In an alternative embodiment, a polyclonal antibody reactive with the antigen may be used to purify the antigen.

In a preferred embodiment, the antigen is purified according to the technique disclosed in Isojima et al., *Clin. Exp. Immunol.*, 49:449–456 (1982) and Isojima et al., *Immunological Approaches to Conception and Promotion of Fertility* (Talwar Ed.), 323–333 (Plenum Publishing 1986), both of which are incorporated herein by reference. The homogenized sperm extract is run through an immunoaffinity chromatography column that contains the monoclonal antibody immobilized upon a solid support, such as Sepharose 4B. The antigen is then eluted from the column by lowering the pH.

In an alternative embodiment, the extract can be run through a reverse phase high pressure liquid chromatography (HPLC) column. The fractions that elute from the column are recovered. The protein components of the various fractions are separated by two dimensional gel electrophoresis. The component that contains the antigen is identified by reacting the blots on the gel with the monoclonal antibody and determining, by immunochemical techniques, which component contains the antigen. The antigen may then be recovered in substantially purified form by known techniques. The method has been verified by microsequencing the amino termini of the purified peptides and the amino acid sequences have been shown to overlap with the amino acid sequences deduced from gene cloning, thus confirming the usefulness of the method.

The substantially purified antigen of the invention may be further purified by various protein purification techniques. The protein purification techniques include those identified and described in U.S. Pat. No. 4,446,122 issued May 1, 1984 to Chu et al., which is incorporated herein by reference. Preferably, the antigen is purified by preparative electrophoresis or affinity purification.

In an alternative embodiment, the antigen of the invention may be isolated and purified from human sperm by general techniques well-known in the art, modified and applied in accordance with the discoveries and teachings described herein. Such techniques include electrophoresis, centrifugation, gel filtration, precipitation, dialysis, chromatography (including ion exchange chromatography, affinity chromatography, immunoadsorbent affinity chromatography, reverse-phase high performance liquid chromatography, and gel permeation high performance liquid chromatography), isoelectric focusing, and variations and combinations thereof.

One or more of these techniques are employed sequentially in a procedure designed to separate molecules according to their physical and chemical characteristics. These characteristics include the hydrophobicity, charge, binding capability, and the molecular weight of the antigen. The various fractions of materials obtained after each technique are tested for the ability to react with monoclonal antibody MHS-10, produced by ATCC HB 10039. Those fractions showing such activity are then subjected to the next technique in the sequential procedure, and the new fractions are tested again. The process is repeated until only one fraction reactive with MHS-10 remains and that fraction produces only a single band when subjected to polyacrylamide gel electrophoresis.

The antigen of the invention may be modified by known protein modification techniques. These include the techniques disclosed in U.S. Pat. No. 4,302,386 issued Nov. 24, 1981 to Stevens, incorporated herein by reference. Such modifications may enhance the immunogenicity or antifertility activity of the antigen or it may have no affect on such activity. For example, a few amino acid residues may be changed or removed. Alternatively, the antigen of the invention may contain one or more amino acid sequences that are not necessary to its immunogenicity or antifertility activity. It may be the case, for example, that only the amino acid sequences of a particular epitope of the antigen will be necessary for immunogenic activity. Unwanted sequences can be removed by techniques well-known in the art. For example, unwanted amino acid sequences can be removed via limited proteolytic digestion using enzymes such as trypsin or papain or related proteolytic enzymes. Alternatively, polypeptides corresponding to various immunogenic epitopes of SP-10 may be chemically synthesized by methods well known in the art. These include the methods disclosed in U.S. Pat. No. 4,290,944 issued Sep. 22, 1981 to Goldberg, incorporated herein by reference.

Thus, the antigen of the invention includes a class of modified polypeptides, including synthetically derived polypeptides or fragments of the antigen, having common elements of origin, structure, and mechanism of action, such as antifertility effect, that are within the scope of the present invention because they can be prepared by persons skilled in the art, once given the teachings of the present invention. This includes any polypeptide derived from the deduced amino acid sequence of FIG. 11A, including fragments and variants of the sequence, that is immunogenic and has an antifertility effect. For example, we have shown that one peptide fragment of SP-10 as shown in FIG. 11A containing 71 amino acids (amino acids 143–213 in FIG. 11A) reacts with the MHS-10 monoclonal antibody. SP-10 may contain other epitopes that react with MHS-10, which can be determined by persons skilled in the art. Accordingly, such polypeptides or peptide fragments are within the scope of the invention. Moreover, since persons skilled in the art can make modifications to or derivatives of such epitopes, such modifications or derivatives are within the scope of the invention, provided that they are immunogenic and have an antifertility or contraceptive effect in humans or other primates or other mammals.

The monoclonal antibody used to identify, characterize, and purify the intra-acrosomal antigen is within the scope of the invention. It reacts with a substantially purified intraacrosomal human sperm antigen that remains associated with the sperm after the acrosome reaction. Preferably, the antibody reacts with a human sperm antigen located in the acrosomal matrix of mature human sperm prior to the acrosome reaction and found in association with the inner acrosomal membrane or equatorial segment after the acrosomal reaction.

The monoclonal antibody of the invention lacks crossreactivity with substantially all human somatic tissues. In addition, the antibody inhibits sperm-egg interactions in the hamster egg penetration test. These characteristics demonstrate reasonably conclusively that the antigen of the invention or the active parts thereof can be expected to have antifertility activity after being injected into a human female.

In a particularly preferred embodiment, the monoclonal antibody of the present invention has the characteristics of the mouse monoclonal antibody produced by the hybridoma cell line ATCC HB 10039 or mutants or variants thereof. ATCC HB 10039 is a biologically pure culture available from the permanent collection of the American Type Culture Collection (ATCC), 12301 Parklawn Drive, Rockville, Md. USA, 20852 and was deposited there on Feb. 28, 1989. The immunoglobulins produced by this hybridoma are of the IgG1 isotype as demonstrated by enzyme-linked immunosorbent assay employing isotype specific reagents.

The monoclonal antibody of the invention is prepared by a modification of the known techniques for the preparation of monoclonal antibodies and hybridomas. The modification reflects the discovery by the inventors that the antifertility antigen of the invention resides in the acrosomal matrix prior to the acrosome reaction but it is then found in association with the inner and outer acrosomal membranes after such reaction. This knowledge permits the modification of the conventional technique to reproducibly provide monoclonal antibodies to antifertility antigens found in association with the inner and outer acrosomal membranes after the acrosome reaction.

Accordingly, the host animal is immunized with either acrosome-reacted human sperm or the supernatant obtained from centrifuging acrosome-reacted human sperm. In the first case, the sperm antigen is then on the surface of the sperm, since it remains associated with the inner acrosomal membrane. In the second case, the supernatant will contain high concentrations of the antigen, since it contains the remains of the outer acrosomal membrane, which also contains the antigen. The supernatant may also contain some of the antigen free in solution, since there is an indication that the antigen may also be free in solution in the acrosomal matrix prior to the acrosome reaction. In both instances, the material injected into the host contains an enriched concentration of the immunogens of interest. Thus, a larger fraction of the antibody-producing cells would be expected to produce the monoclonal antibodies of the invention.

Any host that produces antibodies may be used. Conventionally used animals include rabbits or rodents, such as rats or mice. Mice are preferred for the present invention.

Once the animal has been immunized and sufficient time has passed for it to begin producing antibodies, the antibody-producing cells are recovered. Although any antibody-producing cells may be used, B lymphocytes obtained from the animal's spleen are preferred.

The antibody-producing cells are fused with tumor cells to produce hybridomas. As used herein, the term "tumor cell" includes any cell that is capable of fusing with an antibody-producing cell to produce a hybrid "immortal" cell; i.e., one which is capable of continuous grown in vitro. Preferred tumor cells are antibody-producing cells that have been transformed and which have lost their ability to produce immunoglobulin. Such cells include rat myeloma cells and mouse plasmacytoma cells. Particularly preferred are mouse plasmacytoma cells that are deficient in the enzyme hypoxanthine-quanine phosphoribosyl transferase (HGPRT), which allows the selection of hybridomas from unfused antibody-producing cells or plasmacytoma cells when grown on a medium containing hypoxanthine, aminopterin, and thymidine.

It should be noted that the antibody-producing cell and the tumor cell can be from different animal species. For example, see Nowinski et al., *Science*, 210:534 (1980), which is incorporated herein by reference.

The hybridomas are then screened using acrosome-reacted human sperm or the supernatant obtained from centrifuging acrosome-reacted human sperm in known immunoassays to identify one or more hybridomas that produce the desired monoclonal antibody. Once the monoclonal antibody-producing hybridomas have been selected, the antibodies can be recovered from such hybridomas by known techniques. Generally, it is useful to clone one or more of the monoclonal antibody-producing hybridomas to expand it into a continuous cell line that can be used to produce the monoclonal antibodies of the invention in quantity.

The previously mentioned method of producing the monoclonal antibodies of the present invention is an in vitro method. The present invention also comprises an in vivo process for producing monoclonal antibodies to the sperm antigen. Such antibodies are produced by placing a hybridoma of the invention intraperatoneally into a histocompatible or immunosuppressed animal host, preferably a small mammal and most preferably a mouse. This causes the host to produce ascites tumors which, in turn, produce a fluid that contains monoclonal antibodies produced by the hybridoma. After sufficient time has passed for the antibodies to have been produced in sufficient quantities, they are recovered by known techniques. This is particularly useful for furnishing the monoclonal antibody in commercially useful quantities.

The present invention also includes hybridomas and continuous cell lines that produce the monoclonal antibodies of the invention. Preferably, the hybridomas and cell lines produce monoclonal antibodies to an intraacrosomal antigen that remains associated with the inner and outer acrosomal membranes after the acrosome reaction. Most preferably, the continuous cell lines have the characterstics of the hybridoma cell line having ATCC excession No. HB 10039 or mutants or variants thereof. The invention also encompasses individual cells within these cell lines.

A person skilled in the art can use known techniques to produce mutants or variants of ATCC HB 10039. Such mutants or variants are encompassed within the present invention as long as they produce monoclonal antibodies reactive with the intraacrosomal antigen of the invention. In addition, a person skilled in the art, using known techniques and the teachings disclosed herein, will be able to produce monoclonal antibodies reactive with the antigen of the invention but having slightly different characteristics from ATCC HB 10039 or the antibodies produced by such cell line. Nevertheless, such monoclonal antibodies and the hybridomas or cell lines that produce them are within the scope of the present invention. In a particularly preferred embodiment, the monoclonal antibodies produced by ATCC HB 10039 will prevent such monoclonal antibodies from reacting with the antigen of the invention.

The antigen of the invention, preferably SP-10, can be used to make monoclonal antibodies reactive with epitopes different from the epitope to which MHS-10 reacts. The purified or substantially purified antigen can be used as the immunogen for injecting into the host as previously described in the method for making the monoclonal antibodies of the invention.

Since a variety of different systems and methods might be used to produce a monoclonal antibody reactive with the human sperm antigen of the invention, a variety of monoclonal antibodies may result from these measures that are distinct from the antibody illustrated in the examples below. However such monoclonal antibodies, whose production is enabled by the teachings herein, still clearly within the scope of this invention. The salient feature of such antibodies, for the purposes of this invention, besides their monoclonality, is their reactivity in any way with the human sperm antigen of the invention, regardless of the species of origin, isotype, molecular specificity, affinity, method of production, or particular type of hybridoma employed in their production.

The monoclonal antibody of the present invention may be purified by the use of known techniques in view of the teachings contained herein. For example, ascites fluid containing the monoclonal antibody is mixed with a fractionating material, such as ammonium sulphate, to precipitate immunoglobulins, including the monoclonal antibody of the invention. The precipitate is separated and resuspended in solution. The solution is dialyzed through a membrane to remove the fractionating material, producing a dialysate that contains the monoclonal antibody. The dialysate is then run through an affinity column, such as a protein A Sepharose bead column. The column is washed, and the antibody is eluted by lowering the pH by the use of an appropriate buffer.

The invention also comprises polyclonal antibodies to the human intra-acrosomal sperm antigen. Such antibodies are produced by known techniques, appropriately modified in view of the teachings contained herein. An appropriate amount of the antigen is administered to an animal host to create an immunogenic response. Any host that produces antibodies may be used. Conventionally used animals include rabbits and rodents, such as rats or mice.

Once the animal has been immunized and sufficient time has passed for it to begin producing antibodies, polyclonal antibodies may be recovered by techniques known in the art. The general method comprises removing blood from the animal and separating the serum from the blood. The serum, which contains antibodies to the antigen, may be used as an antiserum. Alternatively, the antibodies can be recovered from the serum. Affinity purification is a preferred technique for recovering purified or substantially purified polyclonal antibodies to the human sperm antigen of the invention.

The preferred method of producing the antigen of the invention is by culturing a proycaryotic cell, such as a bacterium, fungi, or other microorangism, or a eucaryotic cell, such as a yeast or a mammalian cell or cell line, transformed by an expression vector or virus containing DNA that codes for the antigen or any desired part thereof. Preferably, the transformed cell is E. coli or a cell from a Chinese hamster ovary cell line. The expression vector contains a DNA sequence that codes for the antigen or any desired part thereof which has been operably linked to the appropriate regulatory control nucleic acid sequences so that the DNA sequence can be expressed in the transformed cell of choice.

The DNA of the invention is an isolated or substantially purified DNA sequence (i.e., polydeoxyribonucleotide) encoding a polypeptide that comprises the antigen of the invention. As used herein, the term "isolated" and variations thereof means that the DNA is in isolation from DNA encoding proteins normally accompanying this antigen. Thus, the DNA of the invention includes DNA encoding the antigen when that DNA has been cloned into a bacterial vector, such as a plasmid, or into a viral vector that may harbored by a bacteriophage, provided that such clones are isolated from clones that contain DNA encoding other proteins normally accompanying the antigen. As used herein, the term "substantially pure" and variants thereof means that the DNA is substantially free of DNA and RNA that does not encode the antigen of the invention. That is, there will be no more than about 5 percent of other DNA and RNA and preferably no more than about 1 percent of other DNA and RNA in any sample that contains the DNA encoding the antigen of the invention. Preferably, the DNA of the invention is a complimentary DNA (cDNA).

The cDNA of the invention is isolated from a testes cDNA expression library, using known techniques and the disclosure contained herein. See Chang et al., *Science*, 240:324–326 (1988), incorporated herein by reference. An example of such a library is the lambda gt11 testes-specific cDNA library available from Clonetech, Inc. Such a library can be screened with the monoclonal antibody of the invention, using known immunochemical techniques. This permits the identification and subsequent isolation, purification, and sequencing of the cDNA. The SP-10-5A cDNA was sequenced using a Sequenase sequencing kit (U.S. Biochemical Corp.) utilizing the Sanger dideoxy termination procedure (Sanger et al., *Proc. Natl. Acad. Sci.* 74:5463–5467 (1977), incorporated herein by reference).

The genomic DNA of the invention is obtained through the application of known techniques in view of the teachings contained herein. Blots containing human genomic DNA digested with various restriction enzymes have been probed separately with fragments containing the 5' and 3' ends of the SP-10-5 cDNA. The 5' SP-10-5 probe hybridized to a single band of 5 kb while the 3' probe hybridized to a 1.5 kB band. This simple banding pattern suggests that SP-10 is coded for a by a single copy gene or more than a one copy arranged as tandem repeats.

A human leukocyte genomic DNA library (Clontech) was screened with a 634 bp fragment of SP-10-5. Five out of $5\times10^5$ plaques showed strong hybridization to SP-10-5. These plaques were purified and shown to also hybridize to the 3' end of SP-10-5, which suggests these clones contain the entire coding region of SP-10. Chromosomal location studies indicate that the gene for SP-10 is located on chromosome 11, probably in the area of the 11q2 band.

In a particularly preferred embodiment of the invention, the cDNA contains approximately 1.35 Kb and comprises the nucleotide sequence shown in FIG. 11A. FIG. 11A also shows the predicted amino acid sequence of the particularly preferred antigen of the invention, SP-10. In a particularly preferred embodiment, the cDNA contains a 214 base pair fragment of the gene coding for the antigen. This fragment is believed to contain the epitope recognized by the MHS-10 monoclonal antibody produced by ATCC HB 10039. The peptide containing the MHS-10 epitope consists of 71 amino acids extending from amino acid 143 to amino acid 213. This peptide spans a domain of the protein which contains several repeat motifs that have a hydrophilic character.

It will be recognized by persons skilled in the art that the cDNA sequence of the preferred antigen may be modified by known techniques in view of the teachings disclosed herein. For example, different codons can be substituted that code for the same amino acid as the original codon. Alternatively, the substitute condons may code for a different amino acid that will not affect the antifertility activity or immunogenicity of the antigen or which may improve the antifertility activity or immunogenicity of the antigen. For example, site directed mutagensis or other techniques to create single or multiple mutations, such as replacements, insertions, deletions, and transpositions, as described in Botstein and Shortle, "Strategies and Applications of In Vitro Mutagenesis," *Science*, 229:193–1210 (1985), which is incorporated herein by reference, can be employed. Since such modified DNA can be obtained by the application of known techniques to the teachings contained herein, such DNA is within the scope of the claimed invention.

Moreover, it will be recognized by those skilled in the art that a cDNA sequence obtained from a cDNA expression library or prepared from isolated messenger RNA that codes for the antigen of the invention may exhibit the natural allelic variations found among individuals. Since such variant cDNA sequences are obtained by the teachings contained herein, they are within the scope of the invention.

Finally, it will be recognized by those skilled in the art that the cDNA sequence (or fragments thereof) of the invention can be used to obtain other cDNA sequences that hybridize with it under conditions of high stringency, using general techniques known in the art, or used to obtain any DNA that hybridizes with the cDNA under conditions of high stringency. Such DNA includes any genomic DNA. Accordingly, the DNA of the invention includes DNA that shows at least 75 percent, preferably 90 percent, and most preferably 95 percent homology with the genomic DNA coding for the antigen SP-10 or the cDNA of FIG. 11, provided that such homologous DNA encodes the antigen of the invention.

The DNA of the invention may be used in accordance with known techniques, appropriately modified in view of the teachings contained herein, to construct an expression vector, which is then used to transform a microorganism for the expression and production of the antigen of the invention. Such techniques include those disclosed in U.S. Pat. Nos. 4,440,859 issued Apr. 3, 1984 to Rutter et al., 4,530,901 issued Jul. 23, 1985 to Weissman, 4,582,800 issued Apr. 15, 1986 to Crowl, 4,677,063 issued Jun. 30, 1987 to Mark et al., 4,678,751 issued Jul. 7, 1987 to Goeddel, 4,704,362 issued Nov. 3, 1987 to Itakura et al., 4,710,463 issued Dec. 1, 1987 to Murray, 4,757,006 issued Jul. 12, 1988 to Toole, Jr., et al., 4,766,075 issued Aug. 23, 1988 to Goeddel, et al., and 4,810,648 issued Mar. 7, 1989 to Stalker, all of which are incorporated herein by reference.

The DNA of the invention may be joined to a wide variety of other DNA sequences for introduction into an appropriate host. The companion DNA would depend upon the nature of the host, the manner of the introduction of the DNA into the host, and whether episomal maintenance or integration is desired.

Generally, the DNA (preferably the cDNA) is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. Once selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell. The preferred expression vector for use in the invention is pWR 590 and pGEX.

The antigen of the invention or an immunogenic fragment thereof is expected to have utility as an immunogen in an antifertility vaccine for humans and other primates and other mammals. Such a vaccine can be prepared by techniques known to those skilled in the art and would comprise, for example, the antigen, a pharmaceutically acceptable carrier, an appropriate adjuvant, and other materials traditionally found in vaccines. An immunologically effective amount of the antigen or fragment thereof is determined by means known in the art.

The cost effectiveness of expression and scale up of eukaryotic proteins in *E. coli* has made this the model of choice for initial expression of the SP-10 recombinant vaccine. Many low molecular weight proteins expressed in *E. coli* may be rapidly degraded unless these proteins are fused to a large *E. coli* protein. (We have used the pWR590 expression system (Guo et al, Gene 29 (1984), 251–254 incorporated herein by reference) which includes the *E. coli* lac promotor and a portion of the coding sequence for beta-galactosidase which can code for approximately 590 amino acides. The injection of the SP-10 protein attached to this attenuated beta-galactosidase has proven to be strongly immunogenic into rabbits.) In the preferred embodiment genes encoding portions of the entire open reading frame for the SP-10 protein are inserted into a bacterial plasmid containing a strong promotor and a bacterial gene or portion thereof. The expression of the SP-10 protein occurs in conjunction with the bacterial protein and the two proteins are attached through amino acid linkages. Following lysis of the bacteria and purification of the resulting fusion protein using preparative SDS-PAGE or other methods, such a "fusion protein" may afford the advantage that the bacterial protein may function as a adjuvant to enhance the immune response of the host to the recombinant eucaryotic antigen.

The antigen of the invention may also be used in quantitative assays with the monoclonal antibody of the invention for the detection of acrosome-reacted sperm. The purified antigen may be used as a standard or a control. Direct or indirect immunofluorescence can be used to correlate the extent to which human sperm in a sample have undergone the acrosome reaction. This data can be used to develop a standard curve whereby the extent to which human sperm in a sample have undergone the acrosome reaction can be determined by competition or direct immunoassay of SP-10 or other intra-acrosomal antigen obtained from the culture supernatant of the acrosome-reacted sperm and assayed by radioimmunoassay or enzyme-linked immunoassay.

The antigen of the invention can be used to detect and measure antisperm antibodies. The detection of antisperm antibodies has witnessed an array of assay methods over the years, including assays based on agglutination of sperm cells (Kibrick assay), cytotoxicity and immobilization of sperm cells, (Isojima), binding to sperm surface or cytoplasmic antigens (Herr et al, 1987, Am. J. Reprod. Immunol. 11:75-81) using ELISA or RIA formats or the binding of class specific immunobeads (Bronson). These assays are distinguished by the fact that they are targeted to whole cells. To date there has not been a widely used assay for antisperm antibodies that employs single molecular target antigens or groups of these targets antigens. The advent of recombinant methodologies opens the possibility that defined sperm antigens might now be employed as targets for measuring antisperm antibodies. SP-10 is an example of an antigen that may work in this regard.

The antigen of the invention, including polypeptides encoded by the cDNA of FIG. 11, fragments, modifications and derivatives thereof, is also useful in studying fertility and contraception in mammals, especially primates, to better understand human fertility and infertility.

The monoclonal or polyclonal antibodies of the present invention may be used to identify sperm, particularly acrosome-reacted sperm, in various types of samples, such as human semen. The antibodies may be used as a reagent in known immunoassays for determining the presence or concentration of human sperm, sperm heads, or acrosome-reacted sperm. Such immunoassays include, but are not limited to, radioimmunoassay, competition immunoprecipitation assay, enzyme-linked immunoabsorbent assay, and direct or indirect immunofluorescence assay. One application of this approach is the identification of sperm in sexual assault evidence.

A composition for determining the presence or concentration of human sperm or otherwise evaluating sperm in accordance with the present invention contains a concentration of the antibody effective to detect the presence of such material or quantify its amount. The antibody can be mixed with or attached to any suitable carrier, such as a latex particle, a plastic bead, or a plastic microtiter plate. It may also be conjugated with an enzyme or dye or radiolabeled, depending upon what immunological method is employed.

The monoclonal or polyclonal antibodies of this invention are also useful for the isolation or purification of human sperm from complex mixtures or solutions on the basis of a selective immunological reaction. The mixture is brought into contact with immobilized antibodies of the invention, which will separate the sperm from the mixture by forming immobilized complexes of the sperm bound to the antibody. When the mixture is removed, the sperm is separated from the antibodies and recovered in purified form by known techniques. Preferably, the sperm is permeabilized before being contacted with the antibodies.

A composition in accordance with the invention useful for purifying or removing sperm from complex mixture contains an effective amount of the monoclonal or polyclonal antibody of this invention, immobilized on an acceptable matrix or admixture with an acceptable carrier, to permit reaction and binding with the sperm.

The antibodies of this invention are also useful reagents for research into the structure, function, and immunochemistry of human sperm, particularly acrosome-reacted human sperm. A composition in accordance with the present invention useful as an investigational reagent contains an amount of antibody effective to provide the information upon mixture with the sample and subsequent analysis. Determination of the amount of antibody necessary to accomplish a particular research goal depends upon the specific types of investigation involved and is readily within the skill of one engaged in such research.

The monoclonal or polyclonal antibody of the invention, is preferably used in the following diagnostic procedures: (1) as a probe for immature germ cells in semen in order to detect infertility caused by defects in human spermatogenesis; (2) as a marker for the acrosome reaction in human sperm; (3) as the active ligand in a sperm cell affinity bead for isolation of sperm cells for (a) purification of sperm cell DNA for subsequent RFLP analysis with application in forensic science and paternity testing and (b) isolation of acrosome-reacted human sperm for subsequent fertilization of human eggs; and (4) as a probe for identifying sperm heads in material evidence obtained from sexual assaults.

Round cell syndrome refers to the presence of many round cells in semen in addition to spermatozoa. These round cells may be lymphocytes, macrophages, sloughed epithelial cells from accessory sex organs, and germ cells which have not fully matured into spermatozoa. Currently, there are no immunohistochemical probes which selectively identify immature germ cells during analysis of round cells present in semen.

The present invention will allow the numbers of immature germ cells present in a semen sample to be determined. This will permit accurate detection of cases of premature or excessive sloughing of germ cells and hence identify cases where problems are occurring with the process of spermatogenesis. This may be of significance in cases where spermatogenesis is being interfered with by environmental toxins, infections of the male reproductive tract, or alterations in the normal homonal balance of the male. Thus, the invention will allow for a differential diagnosis of round cells in semen, giving a positive identification of some early stages of germ cells.

This will be accomplished by contacting a sample containing human sperm with the monoclonal or polyclonal antibody of the invention, where the antibody has been labeled by known techniques with a detectable entity. The image formed by the antibodies is then evaluated and compared to known or standard images of human sperm at the appropriate state of development.

The monoclonal or polyclonal antibodies of the invention will also be useful as a marker for the acrosome reaction in human sperm. They could be used to assess the number of acrosome reactive or unreactive sperm in a given population. The antibody is contacted with a sample of human sperm for a time and under conditions sufficient for the antibody in any acrosome-reacted sperm to form an antigen-antibody complex. The complex is then detected by known techniques for detecting the label or detectable moiety attached to the antibody. These include direct or indirect immunofluorescence, radioimmunoassay, or enzyme-linked immunoassay. This application may be of use to diagnose infertility, when such infertility is due to defects in the sperm's ability to acrosome react as well as defects in the rate of acrosome reaction.

Currently, forensic laboratories and labs concerned with paternity testing are relying on the powerful techniques of RFLP analysis to identify potential suspects or identify the correct father of a given child. Utilizing DNA obtained from material evidence from victims, from the crime scene, or from the blood of possible parents, the DNA is cut with restriction enzymes and electrophoresed. DNA probes which recognize a series of specific nucleotide sequences within the human genome are then employed to identify specific genetic polymorphism, thus identifying DNA from the crime scene, victim, or suspect or from a parent and a child. One current problem in this field of DNA fingerprinting of sexual assault evidence is the isolation of sperm DNA from the other cellular materials obtained from a sexual assault victim. Cells (such as bacteria, yeast, or cervical, anal, or oral epithelial cells) may contaminate the specimens. The monoclonal or polyclonal antibodies of the invention conjugated to a bead may be used to enrich for sperm cells in such mixtures and thus allow for selective extraction of human sperm DNA.

The acrosome reaction is a necessary prerequisite to fertilization. It is thought that only acrosome reacted sperm can fertilize eggs. Since the antigen of the invention appears to be displayed on the inner acrosomal membrane of acrosome-reacted sperm, an antibody-bead conjugate may be used to selectively adsorb acrosome reacted sperm onto a bead or suitable cell affinity matrix. The sperm might then be removed from the bead or used on the bead, to interact with and fertilize human eggs.

Thus, the invention provides a means for isolating acrosome-reacted human sperm cells. Immobilized monoclonal or polyclonal antibodies of the invention are contacted with a sample containing human sperm cells for a time and under conditions sufficient for the antibody to bind to the sperm cells to form antibody-sperm cell complexes. The complexes are then removed from the sample. Preferably, the bound complexes are washed. The sperm cells are then separated from the antibodies using known techniques to provide the sperm cells as an isolate. Preferably, the antibody is attached to an immunoaffinity bead.

Such a bead might be used as a vehicle to administer a selected population of acrosome-reacted sperm into the uterus or oviduct of infertile women who otherwise ovulate normally but are diagnosed as having "unexplained infertility" (possibly of an immune origin). This would allow for a laboratory technician to circumvent in vivo capacitation and present the woman with a population of acrosome-reacted sperm. Further, the acrosome reacted sperm isolated from the affinity bead might be used in in vitro fertilization with human eggs.

Often sexual assault evidence contains few sperm cells. This is often due to the fact that the evidence is the eluate from a dried swab of a body cavity, resulting in sperm heads which have detached from their tails. The specificity of the monoclonal antibody of the invention for sperm heads and its lack of cross reactivity with other human cell types allows the probe to be employed in analysis of sexual assault evidence to prove the existence of sperm cells.

The monoclonal antibody of the invention is also expected to be useful as an active ingredient in a contraceptive gel, cream, or other composition. An amount effective to create an antifertility effect in a human or other mammal is mixed or otherwise added to a pharmaceutically acceptable carrier, which can then be administered for contraceptive purposes.

It is to be understood that application of the teachings of the present invention to a specific problem or environment will be within the capabilities of one having ordinary skill in the art in light of the teachings contained herein. Examples of the products of the present invention, processes for their production, and processes for the use appear in the following examples.

EXAMPLE 1

Preparation of Monoclonal Antibody MHS-10

Monoclonal antibodies were produced using the procedure of Galfre, et al., *Nature*, 266:550 (1977), incorporated herein by reference. Balb/c female mice were immunized four times with $1 \times 10^7$ thrice washed human sperm in incomplete Freunds adjuvant. Each immunization amounted to three injections of 0.1 ml each, injected intramuscularly and intraperitoneally. The sperm were obtained from blood type O donors. After fusion of the mouse spleen cells with myeloma cell line SP2/0 (Schulman, et al., *Nature* 279:269 (1978), incorporated herein by reference), cells were distributed into 96 well plates containing HAT selection medium. HAT selection medium comprises hypoxanthine, aminopterin, and thymidine. Enzyme-linked immunosorbent assay (ELISA) screening for antibodies was performed 14 to 21 days after fusion by employing $1 \times 10^5$ sperm target cells per well. Hybridomas that elicited positive binding to sperm were expanded and cloned by the limiting dilution method of Galfre et al. Twenty-five stable IgG secreting antisperm hybridoma lines were established.

The antibodies were then tested by indirect immunofluorescence for their ability to bind to human sperm. Indirect immunofluroescent localization of the MHS-10 antigen on ejaculated human spermatozoa was performed according to the methods of Herr et al., *Biol. Reprod.*, 32:695–711 (1985), incorporated herein by reference. One of these hybridomas, ATCC HB 10039, produced an antibody of the immunoglobulin in subclass IgG1 that bound to the acrosome of fixed, permeabilized human sperm.

EXAMPLE 2

Hamster Egg Penetration Test

The MHS-10 antibody has been shown to block the interaction of human sperm with zona free hamster eggs. See Anderson et al., *J. Reprod. Immunol.* 10:231 (1987) and Yangimachi et al., *Biol. Reproduction* 15:471 (1976), incorporated herein by reference. In this test, the zona pellucida of hamster eggs was dissolved by treatment with a protease, and human sperm were subsequently added to the zona free eggs. The ability of the sperm to bind and enter the egg was scored by counting the sperm nuclei lying within the egg cytoplasm. Using this technique, the MHS-10 antibody was found to inhibit the number of sperm interacting with hamster eggs.

EXAMPLE 3

Purification of MHS-10

The antibody was first precipitated as follows. Add 8 mls ice cold saturated ammonium sulfate slowly, dropwise with stirring, to 10 mls ascites fluid representing 380–400 mg total protein. This is allowed to stir in the cold for 3 hours. Centrifuge at 10,000 rpm in Sorvall RC-5B for 20 minutes. Discard supernatant and resuspend pellet in approximately 5 ml dH20. Dialyse for 48 hours at 4° C. against 4 changes of PBS at pH 8.0

A protein A column was prepared as follows. Swell 3 gm protein A sepharose CL-4B (Pharmacia) in about 50 mls PBS pH 8.0 for 20 minutes. Pour swollen gel into disposable syringe fitted with a teflon support and 3-way stopcock. Allow all the excess buffer to be excluded as the column packs by gravity. When all the gel is in the column, wash with at least 50 ml buffer (PBS pH 8.0). Store in PBS and 0.2% sodium azide at 4° C. until ready for use.

The antibody was purified on the protein A column as follows. Mix 2 ml dialysed saturated ammonium sulfate precipitate (representing 4 mls ascites) with protein A Sepharose beads in PBS pH 8.0 and agitate end over end overnight at 4° C. Pour the beads into the column and wash through unbound material with PBS pH 8.0 until the baseline on the UV monitor is flat. Bump with PBS pH 5.5 to elute bound IgG1 antibody. Pump buffer through column at a low flow rate, 0.6 ml/min, since antibody elutes slowly at this pH. Clear column of remaining bound material, including other isotypes of antibody with 0.01M Citrate buffer pH 3.0 with 0.87% NaCl. Finally, re-equilibrate column with PBS pH 8.0 and store with 0.2% sodium azide at 4° C.

A typical purification started with 10 mls ascites fluid representing 380–400 mg total protein. After the SAS precipitate is resuspended in 5 mls $dH_2O$ and dialyzed, the total volume will be approximately 7 mls and the protein concentration 15 mg/ml.

From 75 mg dialyzed SAS precipitate purified on a protein A column, 43 mg will be proteins other than IgG that do not bind to the column (Fraction I), and 32 mg will be pure IgG that elutes with the pH 5.5 PBS (Fraction II). A small amount of immunoglobulin of different subclasses is cleared from the column with the pH 3.0 citrate (Fraction III).

Reloading Fraction I onto the column and eluting again did not yield any additional IgG, indicating that the binding capacity of the column was not exceeded initially with the 75 mg SAS precipitate.

A 10% acrylamide gel was run to confirm the identity of the purified fraction. When 100 ug of protein from the starting ascites, Fraction I, and Fraction II were run on the gel and stained with Comassie Blue, only two bands of heavy and light chain antibody were present in Fraction II and little or none was apparent in the Fraction I of material that did not bind to the protein A column.

EXAMPLE 4

Preparation of Monoclonal Antibodies

Monoclonal antibodies reactive with the head of acrosome reacted sperm may be obtained by immunizing mice with the supernatant resulting from separation of acrosome-reacted sperm from the products of the acrosome reaction. A number of methods may be employed to acrosome react human sperm, including incubation with ionophores, follicular and oviductal fluids, and soluble or intact zona pellucida. The sperm are centrifuged at low speed (50×g) to separate the sperm cells from soluble hybrid vesicles consisting of outer acrosomal membrane and plasma membrane. This supernatant is employed in standard immunization protocols as outlined in Example 1.

EXAMPLE 5

Purification of SP-10

An affinity column was prepared as follows. Cyanogen bromide activated sepharose 4B (Sigma Chemical Co.) was used as the immobilizing phase for the MHS-10 antibody. To prepare the beads, 3.0 g of dry beads were swollen in 1 mM HCl for 15 minutes and then washed in 200 ml of the same. Swollen volume was about 10 ml. The beads were washed with coupling buffer (0.1M $NaHCO_3$, pH 8.3 with 0.5M NaCl) and immediately transferred to 15 ml solution of 32 mg purified MHS-10 in coupling buffer. The mixture was agitated end over end in a 50 ml tube overnight at 4° C.

The beads were then washed free of any unbound material with 100 ml coupling buffer. Unreacted active sites on the beads were blocked by incubating with 0.1M tris, 0.1M glycine pH 8.3 with 0.5M NaCl for 2-3 hours at room temperature.

The column was prepared in a 12 ml syringe with teflon support and 3-way stopcock and washed with coupling buffer again. It was then washed alternately with 0.1M acetate, 0.5M NaCl pH 4.0, followed by coupling buffer, then acetate buffer, and finally equilibrated with 0.1M Hepes pH 8.0 with 0.2% azide for storage.

A BCA protein assay on the material that did not bind to the beads indicated that 2 mg of the original 32 mg did not bind.

The sperm was prepared as follows. Fresh ejaculates were allowed to liquefy for 1 hour and then washed twice with 40 ml Ham's F10 medium with Hepes buffer pH 8.0 by centrifuging at 600×g and discarding the supernatant. Sperm pellets were stored frozen at −80° C. with protease inhibitors (5 mM benzamidine, 1 mM PMSF, 2 ug/ml leupeptin, 2 ug/ml pepstatin).

Prior to purification of antigen, sperm pellets were thawed and dounce homogenized in minimum volume of the buffer in which they were frozen.

The extract of soluble proteins was centrifuged at 10,000×g in the microfuge. Preliminary results indicated that the yield of antigen may be further increased by re-extracting the pellets in 1% SDS and pooling with the initial soluble extract such that the final SDS concentration is 0.25%.

The antigen was purified with an affinity column as follows. Sperm extract is either passed over a 10 ml column with sepharose 4B beads or agitated with the beads overnight at 4° C. to preabsorb any proteins which would nonspecifically bind to the beads themselves. The extract was loaded onto the top of the affinity column, and allowed to recirculate over the column by pumping at 0.6 ml/min overnight at 4° C. Unbound material (Fraction I) was washed from the column with 0.1M Hepes buffer pH 8.0 until baseline on UV monitor was flat. Enriched antigen (Fraction II) was bumped from column with 0.1M Glycine buffer pH 2.2 with 0.87% NaCl, and fractions were collected until the baseline was again flat. Finally, the column was re-equilibrated with Hepes buffer pH 8 and stored at 4° C. with 0.2% sodium azide. The enriched Fraction II may be passed over a third column, which is the affinity column prepared with goat anti-mouse IgG, to remove any MHS-10 antibody that may have been released from the MHS-10 affinity column.

The goat anti-mouse IgG affinity column was prepared with CNBr activated sepharose in exactly the same way as the MHS-10 affinity column described above with the following changes. To prepare a 5 ml column, 1.5 g of dry beads were used. It was incubated overnight at 4° C. with 1.5 mg goat anti-mouse IgG with minimum cross reactivity to human, horse, and bovine serum proteins (Jackson Immunochemical Laboratories, Inc.)

In a typical antigen purification, 40 sperm samples were thawed and extracted as described above. The total volume was 7.8 ml and 100 ul was set aside to determine protein concentration and for gel electrophoresis. Total protein was determined by the BCA procedure to be 68 mg. The extract was preabsorbed with sepharose 4B-200 beads and the resulting volume of 38 mls was then allowed to bind to the affinity column.

Proteins which did not bind to the affinity column were eluted with 0.1M Hepes pH 8.0 and collected as Fraction I. After dialysis and lyophilization, this protein was redissolved in 1.0 ml PBS and the total protein was determined to be 16 mg.

Proteins which did bind to the affinity column were eluted with 0.1M glycine buffered saline pH 2.2 and collected as Fraction II. The total volume of Fraction II was 20 mls. Half of this fraction was further absorbed against the goat anti-mouse IgG column to remove any mouse antibody that might have been released from the affinity column. After dialysis and lyophilization, each half of this purified fraction, absorbed and nonabsorbed, was redissolved in 100 ul PBS. The absorbed half of the fraction contained 39 ug of protein and the nonabsorbed half contained 64 ug of protein. Another 65 ug of protein was present in the Fraction III eluted when the column was reequilibrated with Hepes buffer pH 8.

Other protein not accounted for could have been lost to the system and any of the various steps, including non-specific absorption to the precolumn. The amount unaccounted for in this experiment seemed unusually high perhaps due to the increased number of manipulations. In other experiments without the precolumn or anti-mouse IgG column, yields of approximately 150 ug of enriched Fraction II antigen from 12 ejaculates would be typical.

To visualize the degree of enrichment of the antigen, a 10% minigel was run with 20 ug/lane of starting material sperm extract and the 3 fractions collected from the affinity column. Upon Western blotting, no antigen was apparent in Fraction I, the material which did not bind to the column. Both Fraction II and Fraction III revealed the full array of antigen bands. Anomalous bands, apparently the result of mouse IgG being released from the column itself, were apparent on the null ascites control blot as well as in Fraction III and the non-absorbed Fraction II. The anti-mouse IgG column removed most of this contamination in the absorbed fraction.

Amido black staining of the blot or silver staining of the gel of enriched Fraction II protein typically revealed two bands staining in the MHS-10 region around 30 kD, two other bands around 50 kD and 66 kD, and a very heavy band around 78 kD. The bands higher than 30 kD were considered to be contaminants because they were nonimmunoreactive.

The purified SP-10 antigen analyzed on 2-D gels displayed peptides with molecular weights form 18–34 Kda. Peptide bands of 34, 26, 24, and 18 Kd are then purified to homogenity (90%–98%) by sequential electrophoresis and electroelution. A 10% SDS PAGE gel containing the SP-10 fraction from the affinity column is electrophoresed in one dimension and peptide bands corresponding to the immunoreactive antigen are identified by immunoblot. SP-10 peptides are then cut as strips from the gel. The cut strips are electrophoresed on 12% gels. The peptides are scanned for purity. The peptides are transferred to nitrocellulose membranes by electroelution and may then be elututed for inoculation or subsequent biochemical analysis.

EXAMPLE 6

Purification of Antigen by Reverse Phase HPLC

Purification of SP-10 from Human Serum

Serum from 8 to 12 ejaculates was washed by centrifugation in 25 ml each of Ham's F10 medium, Hepes buffer pH 7.4, two times at 550×g for 10 minutes, and then stored frozen at −20° C. until needed. The sperm was thawed, resuspended in 1–2 ml 0.1% TFA (trifluoroacetic acid), dounce homogenized to extract soluble antigen, and microfuged two times at 13,000×g, then filtered through a 0.22 um filter to remove insoluble material. The soluble extract containing 5–10 mg total protein was fractionated on a Gilson HPLC with a Brownlee reverse phase column, 10 mm×25 cm, packed with Aquapore C-8, 300 A pore size, 7 um silica bead. With a flow rate of 1.5 ml/min, a gradient of 0–80% Solvent B over 50 minutes was run. Solvent A was 0.1% TFA in distilled water and solvent B was 0.1% TFA in 2-propanol. Fractions corresponding to individual peaks were detected at 230 nm and collected manually.

Preparative Gel Electrophoresis

These fractions were lyophilized with a Savant Speed Vac, dissolved in Laemmli sample buffer and separated on a 10% polyacrylamide gel. Proteins were electroblotted for 40 minutes at 500 mAmps (10 mM CAPS buffer, 10% methanol, pH 11.0) onto a PVDF membrane backed up with a second PVDF membrane and a third nitrocellulose membrane to capture proteins passing through the PVDF. The PVDF membranes were stained with Coomassie Blue to identify the proteins present in each fraction while the nitrocellulose were probed with MHS-10 antibody to identify the antigenic bands to be cut from the PVDF blots for sequencing.

Amino Acid Sequencing

Amino acid sequencing was performed in the University of Virginia Protein and Nucleic Acid Sequencing Facility. The N-terminal amino acid sequence was determined using an Applied Biosystems 470 A Gas Phase Protein Sequencer. Dried samples of the MHS-10 immunogen were taken up in 75% formic acid and applied to a glass fiber filter coated with Polybrene. The filter was dried and applied to the sequencer. One cycle of Edman degradation was performed without phenylisothiocyanate (PITC) followed by twenty to thirty cycles with PITC. Cleavage of the N-terminal amino acids was accomplished via gas phase trifluoroacetic anhydride resulting in the formation of anilinothiazolinone derivatives. The PTH derivatives or a mixture of PTH standards was analyzed on Waters 840 HPLC system with an IBM C18 reverse phase column and will be detected at wavelengths of 254 and 313 nm. Two SP-10 peptides, the 30 kD and 18 kD forms, have been isolated and amino acid microsequenced.

The N-terminus sequence of the first 12 amino acids of the 30 kD band was found to be: XTVAEX-TSGEXA. This sequence aligned with the predicted sequence deduced from cDNAs beginning with amino acid number 78. The N-terminus sequence of the first 7 amino acids of the 18 kD band was found to be: XDEQXSG. This sequence aligned with the predicted sequence deduced from cDNAs beginning with amino acid number 140.

EXAMPLE 7

Characterization of the Antigen SP-10

Biochemical and morphological characterization of SP-10 shows an acidic, polymorphic protein which is conserved in the human population. Arising during spermatogenesis within the nascent acrosomes of developing spermatids and localizing within the acrosome of intact sperm, SP-10 is not located on the plasmalemma but becomes exposed on the sperm surface following the acrosome reaction. SP-10 is thus a differentiation marker of acrosome development in the human and an example of an intraacrosomal immunogen exposed prior to fertilization, offering a potential target for immunocontraception. SP-10 has been designated a "primary vaccine candidate" by the World Health Organization Taskforce on Contraceptive vaccines, due to its tissue specificity and evidence that the MHS-10 monoclonal antibody inhibited the sperm/egg interaction in the hamster egg penetration assay.

Materials and Methods

1. Immunocytochemistry of Human Testis

Testes were obtained from elective orchiectomies for prostate carcinoma from patients untreated with steroids. Testes were fixed in 2% formaldehyde in 0.1M phosphate buffer and embedded in paraffin. Ten micron sections were mounted on gelatin coated microscope slides, deparaffinized in a graded series of ethanols and rehydrated in phosphate buffered saline (PBS). Sections were pretreated with 10% normal goat serum for thirty minutes, washed 3× in PBS, and reacted with a 1:1000 dilution of monoclonal antibody MHS-10 or control IgG$_1$ in 1% normal goat serum for 30 minutes. Following washing, sections were treated with 1:100 dilution of goat anti-mouse IgG (Jackson Immunoresearch Laboratories, West Grove, Pa.,) for 30 min, washed thrice and incubated with mouse peroxidase-anti-peroxidase, 1:200, in PBS for 30 min, followed by thrice washing in PBS. Brown reaction product, indicating the location of the SP-10 antigen, was developed with 0.05% diaminobenzidine with 0.015% hydrogen peroxide.

2. Immunofluorescence Microscopy

Motile Sperm. Live ejaculated sperm were incubated 1.5 hr in RPMI 1640 medium with 3.5% BSA at 37° with 5% $CO_2$. $1.5 \times 10^8$ sperm were incubated for 1 hr with MHS-10 antibody at 1:100 or control IgG$_1$ at 1:100 diluted in RPMI. Samples were washed 2× in medium and reacted with a 1:100 dilution of goat anti-mouse IgG-FITC (Jackson Immuno Research Laboratories) for 1 hr. Samples were washed 2× an observed as wet mounts. Fifty percent of sperm were motile at time of addition of primary antibody; 25% at addition of second antibody and approximately 10% were motile at time of scoring 1000 motile cells.

Effect of Tx-100 or methanol permeabilization. $3 \times 10^8$ sperm were washed 3× in phosphate buffered saline (PBS) containing 2 uM phenylmethylsulfonylfluoride. Sperm were fixed 30 min in 3% paraformaldehyde. Aliquots were permeabilized with 0.5% Triton X-100 or 100% methanol for 30 min at room temperature. Unpermeabilized samples were treated with PBS. After washing 2×, samples were incubated with a 1:100 dilution of MHS-10 in PBS for 1 hr at 37° C., followed by a 1:100 dilution of goat anti-mouse IgG. Preparations were washed 2× and mounted in 90% glycerol, 0.25M Tris, pH 7.5 and examined.

Routine method for scoring MHS-10 staining and acrosome reacted sperm. Based upon evidence (see results) that membrane permeablization exposed the SP-10 antigen, the following standard method was developed. Sperm from liquefied semen samples were washed twice in Ham's F10 medium buffered with 0.1M Hepes. For induction of the acrosome reaction, sperm suspensions were capacitated for 3 hrs at 37° in Biggers, Whitten & Whittingham (BWW) medium (Biggers et al., *Methods in Mammalian Embryology* (ed. J. C. Daniel) 1st ed., p. 86, (Freeman, San Francisco, 1971), incorporated herein by reference) with 3.5% human serum albumin (HSA). Samples were acrosome reacted for ½ hr in 10 uM calcium ionophore A23187 in BWW containing 0.3% HSA. Sperm were cytocentrifuged onto a microscope slide, allowed to air dry, and fixed with several drops of 3% paraformaldehyde for 45 min at room temperature. Slides were treated with 100% methanol for 20 min at room temperature and blocked with 10% normal goat serum (NGS) for 15 min. Slides were incubated with a 1:100 dilution of monoclonal antibody MHS-10 in 0.01M phosphate buffered saline, pH 7.4, 1% NGS for 45 min at room temperature, followed by three washes in PBS. A 1/100 dilution of fluorescein isothyocyanate conjugated goat anti-mouse IgG (Jackson Immuno Research) in PBS was employed as a second antibody. Specimens were washed extensively and wet mounted in 90% glycerol, 10% 0.1M Tris, pH 7.5 with orthophenylene diamine added to prevent fading of fluorescence.

3. EM Immunocytochemistry

Testis tissue was fixed in 2% glutaraldehyde, 2% formaldehyde in 0.1M cacodylate buffer, pH 7.3. A portion was post-fixed in 2% osmium tetroxide. Tissue was embedded in Araldite 502. Gold sections were cut on an ultramicrotome and then incubated with 0.2% ovalbumin for 30 min. at room temperature to block nonspecific sites. Monoclonal antibody MHS-10 or control IgG$_1$ was diluted 1:50 in 0.2% ovalbumin and reacted overnight with the sections at 4° C. After exhaustive washing in drops of PBS, sections were incubated for 2 hours in a 1:25 dilution of Protein A gold (Janssen Life Sciences, Piscataway, N.J.). Sections were then washed in PBS and stained for 10 min in 5% uranyl acetate and viewed in a JEOL 100CX electron microscope.

4. Western Blots

Donor sperm were washed in Hams F-10 medium, frozen at −80° C. in the presence of 5 mM benzamidine, 1 mM phenylmethylsulfonylfluoride, 2 ug/ml leupeptin, 2 ug/ml pepstatin and thawed and extracted in 1% SDS. One part extract was added to one part 2X Laemmli buffer (Laemmli, *Nature (Lond)*, 227:680–85 (1970), incorporated herein by reference) in the presence or absence of B-mercaptoethanol. Proteins were analyzed by one and two dimensional electrophoresis according to the procedure of O'Farrell, *J. Biol. Chem.*, 250:4007–21 (1975), incorporated herein by reference. Electrotransfer followed Towbin et al., *Proc. Natl. Acad. Sci. USA*, 76:4350–54 (1979), incorporated herein by reference. The nitrocellulose was blocked in 5% milk in PBS/0.5% Tween-20; incubated in the MHS-10 mAb (1/1000) in PBS/0.5% Tween20, 1% milk overnight at 4° C.; goat anti mouse IgG-peroxidase was employed at 1/5,000 dilution. Control IgG$_1$ monoclonal was also diluted 1/1000. Silver staining of protein spots on 2-D gels followed the procedure of Wray et al., *Anal. Biochem.*, 118:197–203 (1981), incorporated herein by reference.

Results

1. SP-10 is a differentiation antigen of spermatogenesis.

Figure 1B:
FIG. 1B. At higher magnification, both crescent shaped and smaller granular reaction product (arrowheads) are observed in cohorts of similar stage germ cells within a single seminiferous tubule. X 720.
Figure 1C:
FIG. 1C. Tissue section treated with the control murine $IgG_1$ shows no staining. X 180.

SP-10 was found to be expressed at a specific stage of sperm differentiation in the human testis. Immunohistochemical examination of paraffin embedded testes (N=3) exposed to the MHS-10 monoclonal antibody (isotype: IgG$_1$), revealed binding to adluminal spermatids and mature sperm within the seminiferous tubules (FIG. 1A, B). Control sections of human testis incubated with another IgG$_1$ monoclonal antibody (FIG. 1C) showed no immunoreaction product. Within round spermatids, immunostaining was frequently observed in crescent shaped structures as well as smaller ovoid granules (FIG. 1B, arrowheads). Groups of similarly stained spermatids which demonstrated either crescent shaped or granular immunoreaction patterns (as in FIG. 1B) were observed in cross sections of single seminiferous tubules. This finding is consistent with previous observations in the human testis that germ cells in several stages of differentiation may coexist in any cross section of a seminiferous tubule. Not all regions of the seminiferous epithelium demonstrated staining, suggesting either a lack of expression of SP-10 in some stages of spermatogenesis or possible detachment of some cells from the seminiferous epithelium in the paraffin embedded material. Basal spermatogonia, Sertoli cells, spermatocytes, and cells within the testicular interstitium showed no immunoreactivity.

2. SP-10 resides within the acrosome of intact sperm.

Figure 2A:
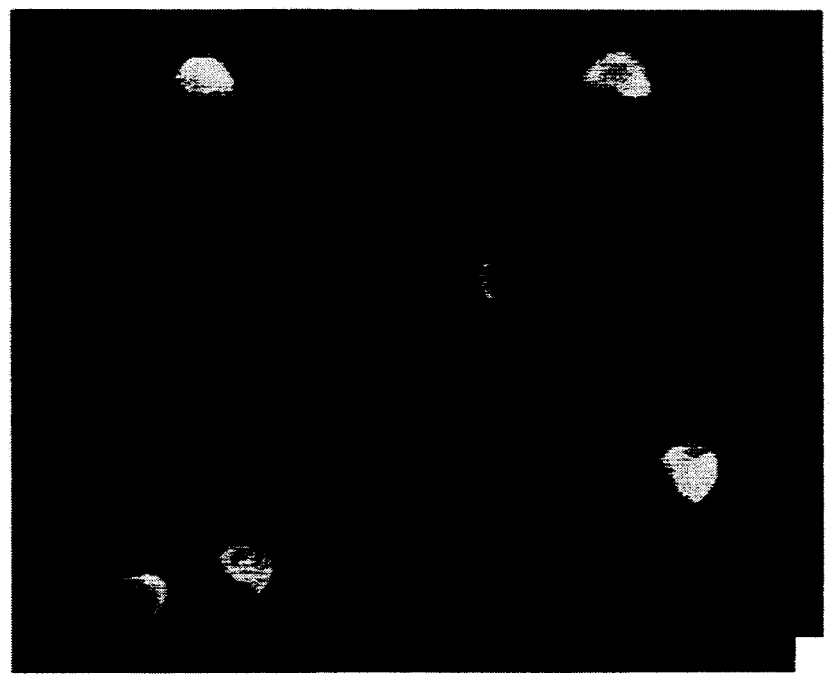
FIG. 2A. A combination phase contrast and fluorescent image demonstrates cap-shaped fluorescence over the anterior portion of the sperm head. X 2870.

By immunofluorescence microscopy, SP-10 localized to the human sperm head. Motile, nonpermeabilized sperm (N=1000) which were incubated with the MHS-10 monoclonal antibody and reacted with a fluorescent secondary anti-mouse antibody showed no immunofluorescent staining of the sperm (data not shown). This indicated that SP-10 was not present on the surface plasma membrane of intact sperm at detectable levels. Sperm which were air dried on slides, fixed with 3% paraformaldehyde, permeabilized with 0.5% Triton X-100 or methanol, and then reacted with the monoclonal antibody and a fluorescent secondary anti-mouse antibody, stained in a cap-shaped fluorescent pattern. This pattern, similar to the known morphology of the acrosome, occurred in >90% of sperm in each sample (FIG. 2A). These results indicated that membrane permeabilizing treatments rendered SP-10 accessible to antibody binding.

3. Ultrastructural localization indicated SP-10 is associated with the acrosomal membranes.

Figure 3:
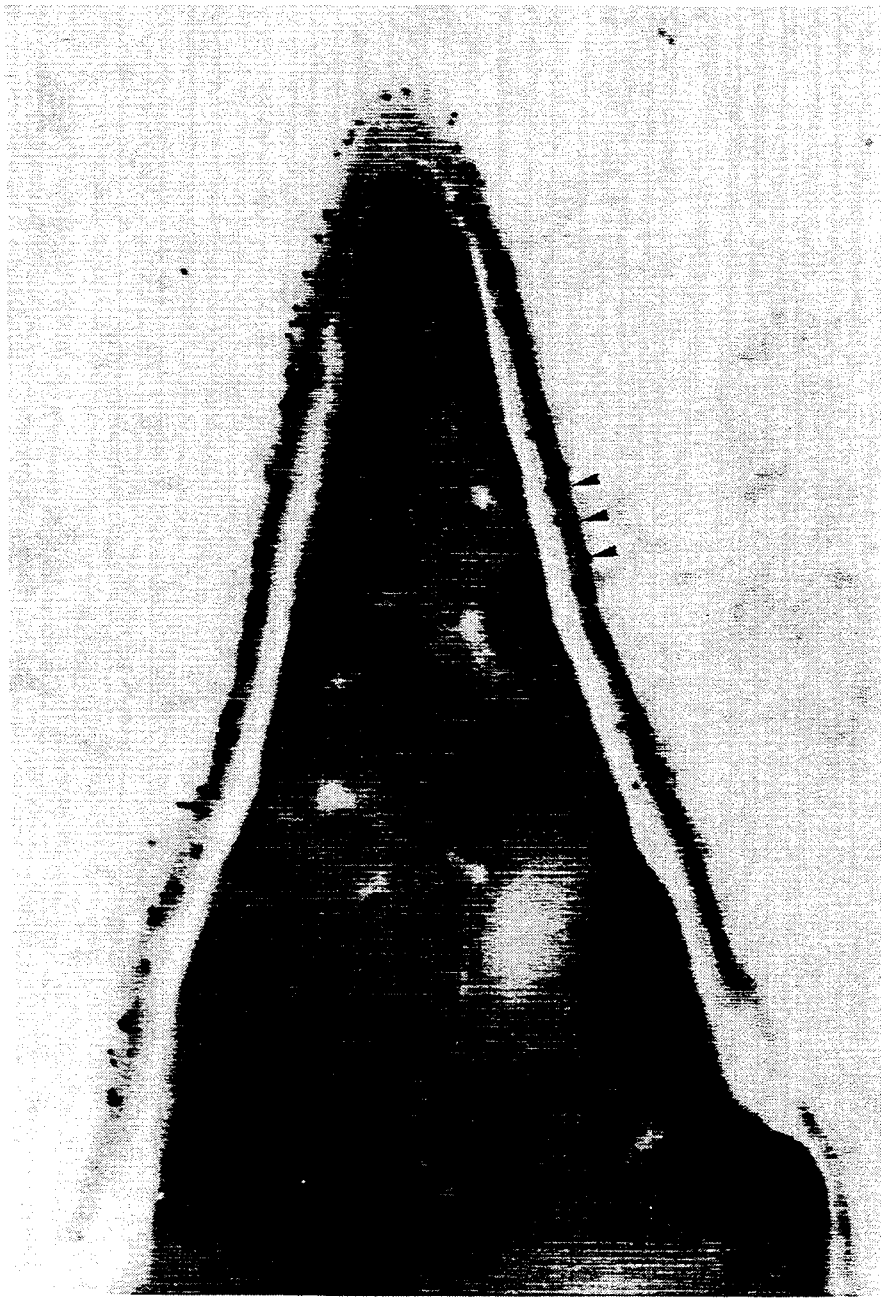
FIG. 3. Electron micrograph of human sperm head following reaction with monoclonal antibody MHS-10 and Protein-A gold. Gold particles are observed over the acrosomal compartment. In regions where the acrosome was sectioned obliquely as at the sperm apex, the gold particles follow a bilaminar distribution. Arrowheads indicate location of acrosomal membranes which are electron lucent in this unosmicated material. X 98,300.

Fine structural studies were performed to localize SP-10 at higher resolution. Mature ejaculated spermatozoa were fixed in 2% paraformaldehyde and 2% glutaraldehyde, prepared for electron microscopy, and immunolabelled on plastic sections with the MHS-10 monoclonal antibody and 10 nm gold particles coated with Protein-A. A concentration of gold particles was observed over the acrosomal compartment (FIG. 3). In sections where a portion of the acrosome was sectioned obliquely (as in FIG. 3 at the sperm apex), gold particles were observed in a bilaminar array. This suggested that in mature, intact sperm, SP-10 is nonuniformly distributed within the acrosome and is associated with the inner and outer acrosomal membranes. Precise assignment of antigen location at the fine structural level was difficult in these preparations because post-fixation in osmium tetroxide, which defines cellular membranes, was found to destroy antigenicity. However, by comparing nonosmicated, immunolabelled specimens to osmicated sperm, the position of the acrosomal membranes was determined to correspond to the electron lucent regions indicated at the arrowheads in FIG. 3. This led to the conclusion that SP-10 is located on the faces of both inner and outer acrosomal membranes adjacent to the acrosomal matrix in mature, intact, ejaculated sperm.

4. Biochemical characterization

Figure 4A:
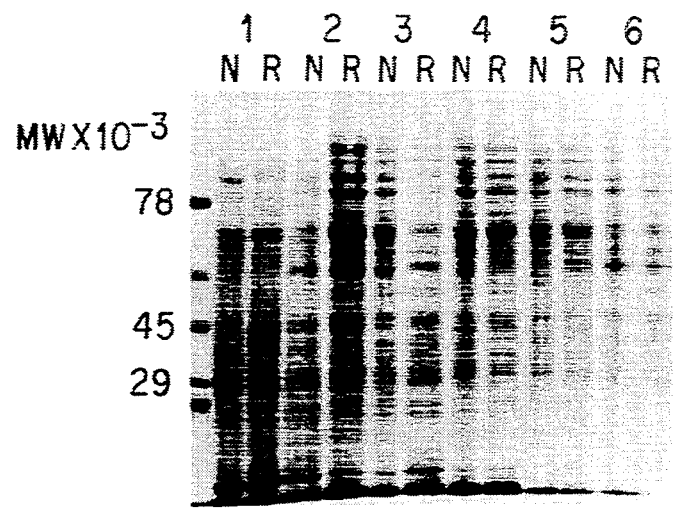
FIG. 4. One dimensional SDS-PAGE gel (10% acrylamide) nitrocellulose electroblot stained with amido black (A) and identical nitrocellulose sheet reacted with the MHS-10 mAb (B) or control $IgG_1$ (C). Sperm extracts from 6 donors (1–6) contained B-mercaptoethanol (lanes marked R=reduced) or lacked this agent (nonreduced=N). 25 ug protein was run per lane. The pattern of SP-10 immunoreactive peptides is identical both between persons and in reduced and non-reduced extracts.
Figure 4B:
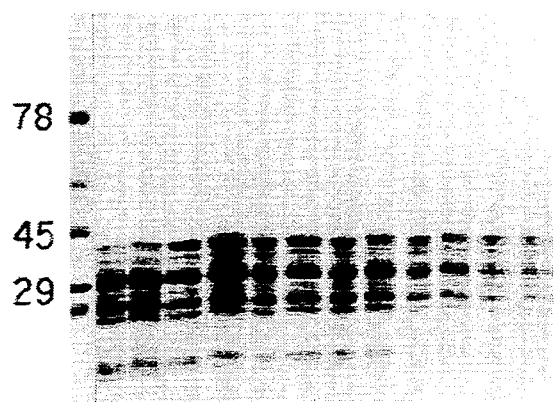
Figure 4C:
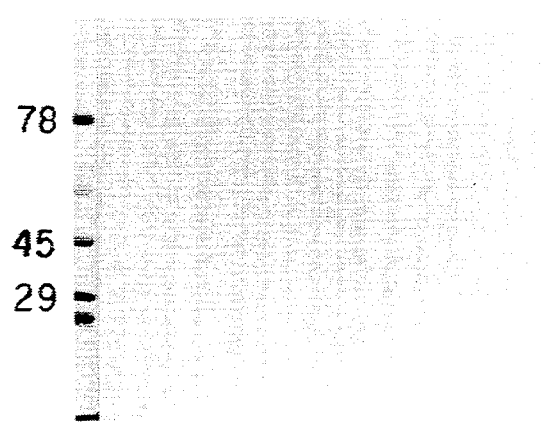

The molecular characteristics of SP-10 were studied by Western blots of one and two dimensional gels on which sperm homogenates were elecrophoresed. The pattern of immunoreactive sperm proteins observed on Western blots of a 10% acrylamide, one dimensional SDS-PAGE gel allowed resolution of at least 14 distinct peptide bands (FIG. 4B), which ranged from 18–34 kDa. Sperm homogenates which were treated with SDS and the disulfide bond reducing agent, B-mercaptoethanol, were compared to homogenates that were not exposed to the reducing agent (FIG. 4B). The pattern of immunoreactive peptides was identical whether or not B-mercaptoethanol was present, indicating that reduction of disulfide bonds did not alter the apparent molecular weights of the immunoreactive peptides.

Figure 5A:
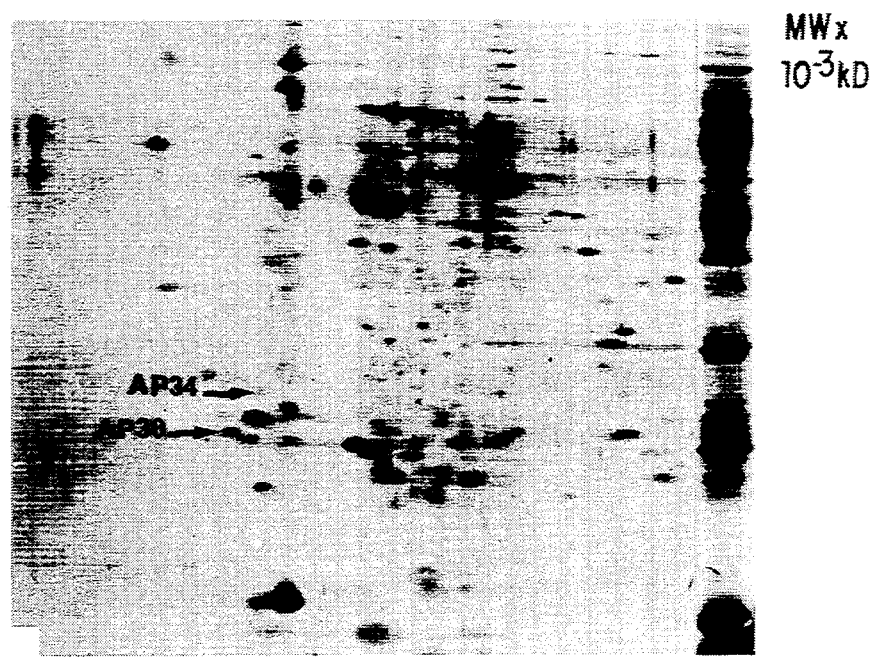
FIG. 5. Silver stained two dimensional gel (A) and immunoblot (B) using MHS-10 mAb on proteins extracted from human sperm. A one dimensional lane showing the silver stain and immunoblot pattern of the sperm extract lie at the right of each figure. Molecular weights (MW) and isoelectric points (pI) are indicated on the right and bottom margins, respectively. Arrows on the silver stain above indicate the location of SP-10 proteins (AP) at 34 and 30 kDa which may be compared to bands and spots of similar mass on the immunoblot below. 2-D and 1-D gels were loaded with 75 and 15 ug of sperm protein, respectively. Immunoreactive SP-10 peptides from 24–34 kd have a pI of 4.9, the 18 kd spots range in pI from 5.1–5.4.
Figure 5B:
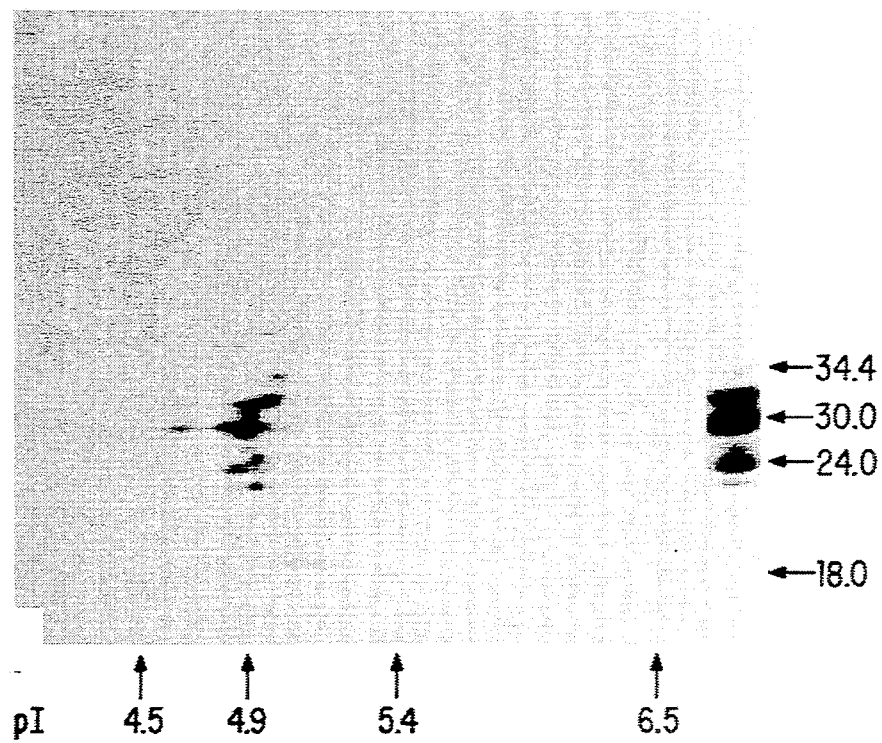

Silver stain of a sperm homogenate which was electrophoresed on a 2-D gel showed many protein spots possessing isoelectric points over the pH range 4.3 to 6.5 (FIG. 5A). The MHS-10 monoclonal antibody immunoreacted (FIG. 5B) with a series of peptide spots which ranged in apparent molecular weight from 18 to 34 kDa. Immunoreactive peptides with apparent molecular weights from 24–34 kDa had isoelectric points of approximately 4.9, while the immunoreactive peptides in the 18 kDa range were slightly more basic with pIs from 5.1–5.4.

5. All individuals tested have the SP-10 protein.

FIG. 4B shows that immunoreactive SP-10 from different individuals was very similar. The relative intensity of antibody reactivity with any one peptide band was similar in different individuals, as was the presence in each sperm homogenate of the full complement of 14 distinct immunoreactive peptide bands. To date, no sperm sample tested, using either immunofluorescence or western blots (N=60), has failed to react with the MHS-10 monoclonal antibody, indicating that SP-10 is highly conserved in the human population.

6. SP-10 remains associated with the sperm head following the acrosome reaction.

Figure 2B:
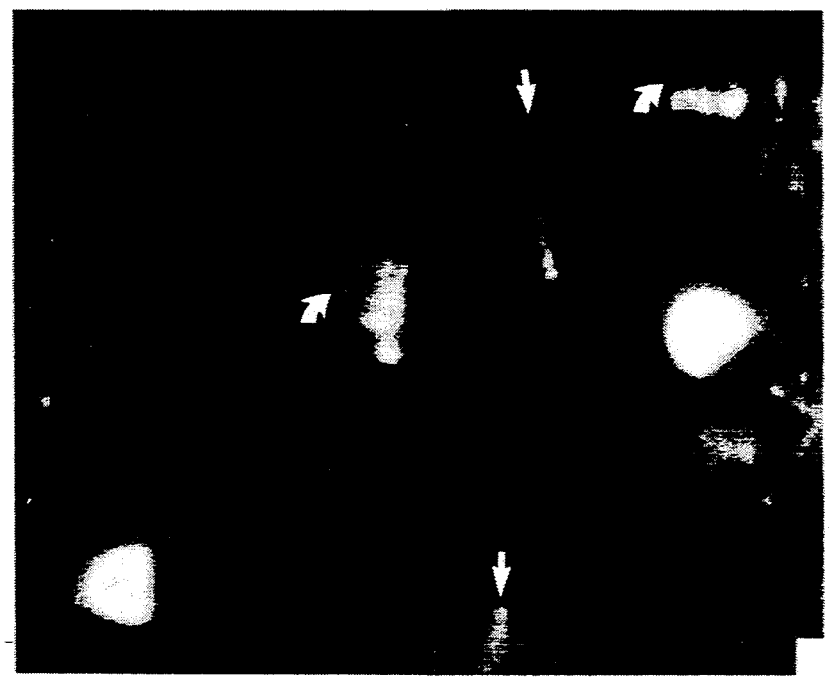
FIG. 2B. Sperm following artificial induction of the acrosome reaction with the calcium ionophore A23187. In the experiment from which the above photo was taken, 47.5% of sperm showed full fluorescent caps, 20.3% faint fluorescent caps (curved arrow), 22.4% equatorial bars (straight arrow), and 9.9% of the sperm were unstained. X 3350.

It is well known that certain constituents of the acrosomal matrix diffuse from the acrosome during the acrosome reaction, when the outer acrosomal membrane fuses with the sperm plasma membrane. FIG. 2B shows immunofluorescent staining patterns obtained when the MHS-10 monoclonal antibody was reacted with sperm samples which had been treated with the calcium ionophore A23187, which induces some of the sperm to undergo the acrosome reaction. Ionophore treated populations contained increased numbers of sperm showing equatorial bars (FIG. 2B, thin arrowheads) as well as sperm displaying either faint caps or faint caps and equatorial bars together (FIG. 2B, thick arrowheads).

These light microscopic results indicated that SP-10 remains, in part, associated with the sperm head following the acrosome reaction. The faint caps suggested that SP-10 persists on the inner acrosomal membrane, which is exposed on the sperm head following the acrosome reaction, while the fluorescent equatorial bars indicated retention of SP-10 in association with the sperm's equatorial segment.

Discussion

The observations that the MHS-10 monoclonal antibody reacts with only round spermatids and subsequent stages of spermiogenesis on testis sections and localizes within the acrosome at the EM level, coupled to the report that somatic tissues were non-reactive with the MHS-10 monoclonal antibody (Anderson et al., *J. Reprod. Immunol.*, 10:231–57 (1987), incorporated herein by reference) together indicate that SP-10 may be classified as a "differentiation antigen," i e. a tissue specific molecule expressed at a precise stage of human spermatogenesis. MHS-10 immunoreaction product was evident in the seminiferous epithelium as small ovoid granules adjacent to the nucleus of round spermatids. This staining, indicative of the earliest stage of spermatogenesis at which SP-10 was detactable, likely corresponds to the nacent acrosomal vesicle and/or perinuclear Golgi region. The MHS-10 monoclonal antibody thus may offer a useful marker of acrosome development in the human. One clinical application of this antibody probe may be in the diagnosis of the incidence of immature germ cells (Golgi phase spermatids and subsequent steps) in semen samples with so-called "round cell syndrome." See Jassim and Festenstein, *J. Reprod. Immunol.*, 11:77–89 (1987), incorporated herein by reference.

The absence of cross reactivity in somatic tissues coupled with its stage specific expression during germ cell differentiation is also germane to the possible utility of SP-10 as a contraceptive vaccine immunogen. Potential problems of autoimmunity, which would be anticipated if common somatic antigens were utilized as vaccine immunogens, may not be found with SP-10.

The immunofluorescence evidence indicated that in acrosome intact, membrane permeabilized sperm, SP-10 localized in a capshaped immunofluorescent pattern that appeared to encompass the entire extent of the acrosome in 90% or more sperm from a given donor. There was no evidence that the MHS-10 antibody recognized its cognate antigen on the plasmalemma of living sperm. The report of the WHO workshop (Anderson et al., *op. cit.* 1987, p. 249) had concluded that the MHS-10 antibody (S20) showed "reactivity . . . with abundant surface antigens on mature sperm." The results reported herein do not agree with this conclusion for acrosome-intact sperm, obtained from populations containing few acrosome-reacted sperm.

Our results show that after ionophore induced acrosome reaction, an increase was noted in the number of sperm displaying fluorescent bars or fluorescent bars together with fainter fluorescent caps. We interpret the reduced immunofluorescence of the cap (faint cap) to indicate that, following the acrosome reaction SP-10, remains displayed on the sperm surface most likely in association with the inner acrosomal membrane. The retention of immunofluorescence after the acrosome reaction in a belt-like bar likely represents retention of SP-10 within the equatorial segment. The equatorial bar immunofluorescence, although covering a much smaller region than the fluorescent cap, appeared to be of the same intensity as the complete cap pattern, indicating that the amount of SP-10 within the equatorial segment is similar before and after the acrosome reaction. The immunofluorescence data was not of sufficient resolution, to determine whether SP-10 remains localized to the inner and/or outer acrosomal membranes and matrix of the equatorial segment or possibly all of these subdomains following the acrosome reaction, or redistributes to include the plasma membrane overlying the equatorial segment.

The WHO sponsored multicenter study presented evidence that the MHS-10 monoclonal antibody (S20) inhibited sperm egg interactions in the hamster egg penetration test. Our model to explain this result postulates that, although sequestered within the limits of the acrosomal membranes in intact, non-acrosome-reacted sperm, the SP-10 antigen is accessible to the actions of the MHS-10 antibody following the acrosome reaction.

A common assumption regarding selection of appropriate sperm immunogens for contraceptive vaccine development is that the target molecules should be surface components accessible to humoral or cellular immune effectors. Although the intraacrosomal localization of the SP-10 peptides in the mature, non-acrosome-reacted sperm appears at first glance not to fulfill this caveat, the remodeling of the sperm head membranes that accompany the acrosome reaction opens the possibility that as a class, constituents of the acrosome, although sequestered from the immune system in intact sperm, should not be dismissed as candidates for contraceptive vaccines without examination of their fate following the acrosome reaction.

Studies with guinea pig sperm have provided remarkable evidence that full but reversible contraception can be achieved by immunizing female animals with the purified sperm protein, PH-20. See Primakoff et al., *Nature*, 335:543–46 (1988), incorporated herein by reference. This molecule of 64,000 daltons is present on both the plasma membrane and, following the acrosome reaction, the inner acrosomal membrane of guinea pig sperm. See Primakoff et al., *J. Cell. Biol.*, 101:2239 (1985); Myles et al., *J. Cell. Biol.*, 99:1634 (1984); Cowan et al., *J. Cell. Biol.*, 103:1289 (1986); and Primakoff et al., *Biol. Reprod.*, 38:921 (1988), all of which are incorporated herein by reference. PH-20 may play a role in sperm binding to the zona pellucida and appears to undergo proteolysis during the acrosome reaction. Antiserum to the PH-20 protein from guinea pig sperm, however, does not cross react with human sperm (Primakoff, personal communication). Although SP-10 and PH 20 appear to be different molecules based upon consideration of apparent molecular weight and immunoreactivity, they share the property of persistence on the sperm head following the acrosome reaction. The remarkable effectiveness of PH 20 in eliciting a contraceptive effect in guinea pigs indicates similar contraceptive potential for SP-10 in humans.

A number of methods, including monoclonal antibody and lectin probes as well as multiple dye techniques, have been utilized to score the acrosome reaction. See Lee et al., *Fertil. Steril.*, 48:649–58 (1987); Berger et al., *Biol. Reprod.*, 40:525–30 (1989); Cross et al., *Gamete Res,*, 15:213–26 (1986); and Wolf et al., *Biol. Reprod.*, 32:1157–62 (1985), all of which are incorporated herein by reference. Because the MHS-10 monoclonal antibody is directed to an intra-acrosomal antigen which changes from a cap shaped immunofluorescence pattern to a faint cap and/or bar during the acrosome reaction, it may also be useful clinically in assessing acrosomal status.

We observed a high degree of similarity between individuals in the immunoreactive forms of SP-10 on Western blots, as well as consistent immunofluorescent localizations on each individual's sperm, indicating that SP-10 is conserved in the human population. This knowledge is essential in choosing a contraceptive vaccine molecule, because it must be present on most, if not all sperm, in order for a vaccine to achieve the widest possible effectiveness. The multiple forms of SP-10 peptides that are identified by Western blotting may represent post-translational modifications, proteolytic processing of the protein within the acrosome, multiple gene products, or several of these possibilities acting in concert. The high degree of similarity between individuals on Western blots suggests that whichever of these alternatives is acting to produce the polymorphism in antigenic peptides, the mechanisms are operating similarly in different individuals. The fact that reduction did not alter the pattern of immunoreactive SP-10 peptides suggests a lack of interchain and few or no intrachain disulfide bonds in SP-10.

The electron microscopic localizations in intact, ejaculated human sperm indicate that SP-10 is asymetrically disposed within the acrosomal matrix, associating in many sperm with the faces of both inner and outer acrosomal membranes adjacent to the acrosomal matrix. Because the polymorphism of SP-10 is not completely understood at the level of amino acid sequence and a function for the SP-10 polypeptides has not yet been determined, aside from their potential as vaccine immunogens, an understanding of the significance of the apparent asymmetry of SP-10 in the acrosome can only be discussed in a general sense. Knowledge of the spatial organization of various molecules within the acrosomal matrix and acrosomal membranes in intact and acrosome reacted sperm is currently in its infancy. The evidence suggests that SP-10 may be a component of such an acrosomal "lamina" in human sperm. Moreover, its asymmetrical distribution in the acrosomal matrix may indicate the molecule contains a hydrophobic domain that directly inserts into the acrosomal membranes.

In summary, by one and two dimensional immunoblots, we showed that SP-10, extracted from ejaculated human sperm, demonstrated a polymorphism of immunogenic peptides from 18-34 kDa, a pattern which was conserved from individual to individual and was not altered by reducing agents. The majority of the antigenic peptides possessed isoelectric points of approximately 4.9. Immunocytochemistry on testis sections indicated SP-10 localized to round spermatids and spermatozoa within the adluminal compartment of the seminiferous epithelium. Immunofluorescence showed that SP-10 was not associated with the surface of acrosome intact, ejaculated sperm. Light and electron microscopic immunocytochemistry localized SP-10 throughout the acrosome, and EM evidence demonstrated a bilaminar array association with the inner aspect of the outer acrosomal membrane and the outer aspect of the inner acrosomal membrane. Following induction of the acrosome reaction with the ionophore A232187, SP-10 remained displayed on the sperm head in association with the inner acrosomal membrane and equatorial segment. The results indicate that the MHS-10 monoclonal antibody may be utilized as a marker of acrosome development in the human and as a probe to evaluate acrosome status. The results also support the hypothesis that inhibition of sperm-egg interaction by anti-SP-10 monoclonal antibody may occur as a result of antigen exposure following the acrosome reaction.

The testis specificity and stage specific expression of SP-10, its conservation in the human population, the ability of the MHS-10 monoclonal to inhibit fertilization in the hamster egg test, and preliminary evidence suggesting that SP-10 remains associated with the sperm head following the acrosome reaction, suggests the utility in this human sperm molecular as a contraceptive vaccine.

EXAMPLE 8

Identification of Human Acrosomal Antigen SP-10 in Primates and Pigs

The intra-acrosomal localization of SP-10 has led to speculation as to the molecule's function. Because the apparent molecular mass of the beta and gamma forms of acrosin (Polakoski and Parrish, *J. Biol. Chem.*, 252:1888–94 (1977), incorporated herein by reference) as well as sperminogen (Siegel et al., *Biol. Reprod.*, 36:1063–68 (1988), incorporated herein by reference) overlap with the apparent mass of SP-10, the question of similarity between SP-10 and these two previously described intraacrosomal molecules has arisen. In this study, we utilize purified preparations of pig acrosin and sperminogen (gifts of Kenneth Polakoski) to demonstrate that although SP-10 is present in pigs, it is distinct from acrosin and sperminogen.

Because SP-10 was first defined as a human sperm antigen, the identification of this molecule in other species will establish a model for testing the anti-fertility potential of an SP-10 based contraceptive vaccine. Employing Western and Northern blots, we demonstrate that primates and pigs are potential animal models for the study of SP-10.

Materials and Methods

1. Sperm Extracts

Human Sperm. Sperm obtained from donor ejaculates were washed in Ham's F-10 medium and frozen at −80° C. in the presence of 5mM benzamidine, lmM Phenylmethylsulfonylfluoride, 2 ug/ml leupeptin, and 2 ug/ml pepstatin. After thawing and extraction in 1% SDS, one part extract was added to one part 2X Laemmli buffer (Laemmli, *op. cit.*) in the presence or absence of B-mercaptoethanol.

Primate Sperm. Sperm were obtained at the University of Washington Regional Primate Research Center from the cauda epididymides of *Macaca mulatta, Macaca fascicularis,* and *Papio cynocephalus anubis* at sacrifice. The caudae were placed in 10 ml of Human Tubal Fluid (Irvine Scientific, Irvine, Calif.), minced into small pieces to allow sperm to escape, and incubated for 15 min. at 37° C., and the resulting suspension was placed in a 15 ml conical centrifuge tube for 5 min. to allow tissue debris to settle. The supernatant containing sperm was decanted and centrifuged at 1,000×g. The pellet was suspended in 500 ul of Laemmli buffer without B-mercaptoethanol and immediately frozen for later shipping. Upon receipt, samples were diluted 2:1 in 4X Laemmli buffer with B-mercaptoethanol.

Sperm of Other Species. Rabbit sperm were obtained via an artificial vagina and were a gift from the laboratory of Eugene Oliphant. Bull sperm obtained by electroejaculation were also a gift from the laboratory of Dr. Oliphant. Rat, pig, and guinea pig sperm were obtained from the cauda epididymides of these species as outlined above with the exception that following centrifugation after collection, these sperm preparations were immediately extracted with 1 ml of 1% SDS and 1% B-mercaptoethanol per $10^8$ sperm.

Protein determinations were performed with the method of Tan, *Anal. Biochem.*, 86:327-331 (1978), incorporated herein by reference. Gels were loaded with 10 ug sperm extract per lane.

2. Western blots

Sperm extracts were electrophoresed on 10% PAGE-SDS gels and electrotransferred at 100 mAmps for 12 hours following the procedure of Towbin et al., *op. cit.* The nitrocellulose was blocked in 5% milk, 2.5% Tween-20; 1% BSA, 0.5% goat serum and 0.15% gelatin (blocking solution) for 30 min. at room temperature. Nitrocellulose strips were incubated in the MHS-10 mAb (1/1000 or 1/2000) or control IgG1 (1/1000) in a 1/5 dilution of the blocking solution (incubation solution) overnight at 4° C. Following a 3X wash in the incubation solution the secondary antibody, goat antimouse IgG-peroxidase, was employed at 1/10,000 dilution on the blots for 2 hours at room temperature. Blots were then washed 3X in PBS and developed with 0.05% DAB and 0.01% $H_2O_2$.

3. Northern Blots

Labelled Probe. The open reading frame for SP-10 has been determined by assembling two overlapping cDNAs cloned from human testis by initially screening a testis expression library with the MHS-10 monoclonal antibody. See Example 9. The open reading frame consists of 795 nucleotides encoding a protein of 265 amino acids. A fragment consisting of 634 bp of the open reading frame for SP-10, produced due to an internal EcoR1 site, was nick-translated (Bethesda Research Labs, Rockville, Md.) with $p^{32}$ dCTP (ICN) and used to probe poly A+RNA on Northern blots.

*Testis RNA.* Human testes were obtained from patients undergoing surgical orchiectomy for prostate cancer. Baboon (*Papio papio,* and *Papio cynocephalus anubis*) and rhesus (*MaCaca fascicularis*) testes were obtained frozen from the University of Washington Regional Primate Research Center. Poly A+RNA was isolated from these tissues using Oligo(dT)-Cellulose Type 3 (Collaborative Research, Inc., Bedford, Mass.). One microgram of human testes, two ug of human liver and placenta, and 10 ug of baboon, rhesus, dog, and cat testis poly A+RNA were electrophoresed on a 1% formaldehyde-agarose gel according to Lehrach et al., *Biochem.,* 16:4743–51 (1977) and Goldberg, *Proc. Natl. Acad. Sci. USA,* 77:5794–98 (1980), both of which are incorporated herein by reference. Final membrane washes consisted of 0.1 X SSPE, 0.5% SDS at 65° C.

Results

Figure 6:
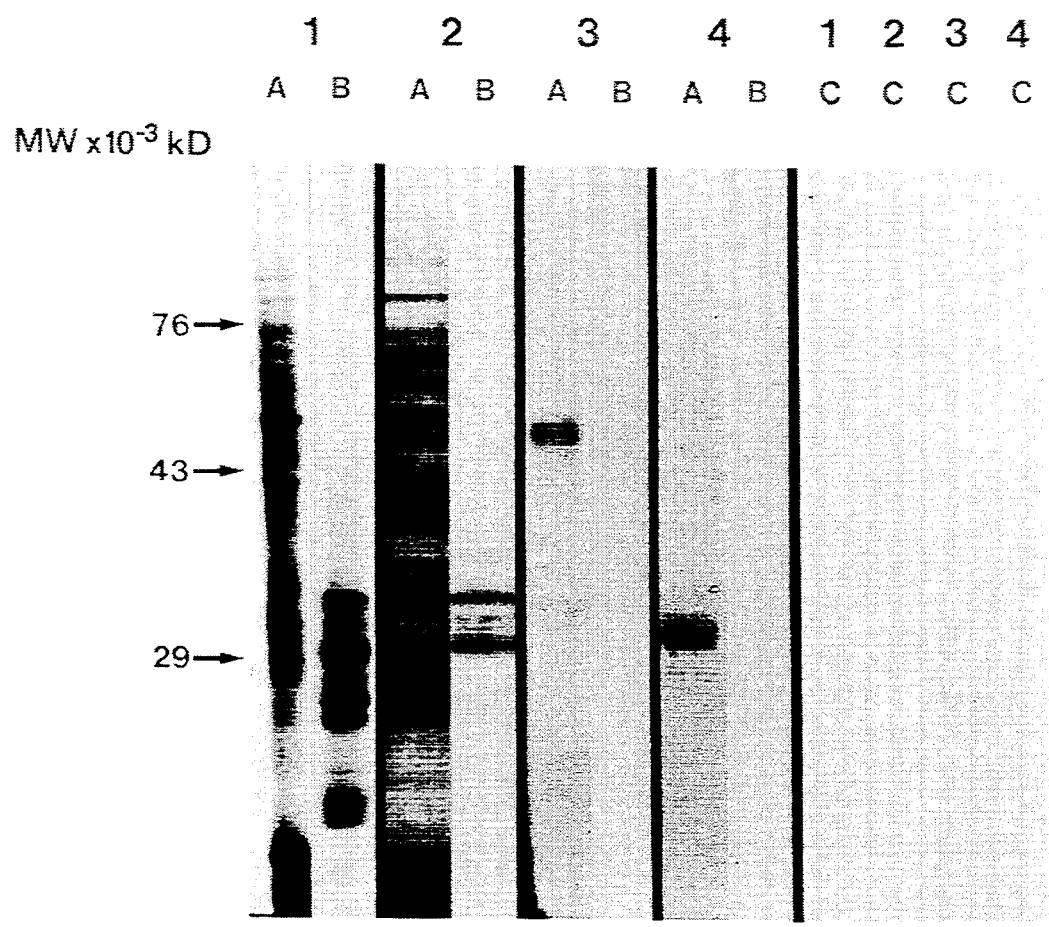
FIG. 6. One dimensional SDS PAGE (16 cm gels) electroblots stained with Amido black (A) and with MHS-10 antibody (B). Lanes 1A & B contained 20 ug human sperm proteins; lanes 2, 80 ug boar sperm proteins; lanes 3, 20 ug purified boar proacrosin; lanes 4, 15 ug purified boar sperminogen. Monoclonal antibody MHS-10 (1/1000) recognized several peptides of similar mass as human sperm SP-10 peptides within the boar sperm homogenate (lane 2B) but did not cross react with purified boar acrosin (lane 3B) or sperminogen (lane 4B). Control lanes 1–4C were reacted with another IgG1 monoclonal antibody ascites.

Immunoblots of proteins extracted from boar sperm demonstrated that the MHS-10 monoclonal antibody recognized several sperm proteins in this species (FIG. 6, lane 2B). Peptides at 34 kDa, 29 kDa and several fainter intermediate bands were recognized in both boar and human sperm by the MHS-10 monoclonal antibody. Interestingly, the immunoblot of boar sperm protein extracts did not demonstrate several of the peptides below 29 kDa which were evident on the immunoblot of the human sperm extract.

Previous studies have reported purification of the boar acrosomal proteins acrosin, Polakoski and Parrish, *op. cit.,* and sperminogen, Siegel et al., *op. cit.* The kind gift of purified boar sperminogen and boar acrosin by Dr. Kenneth Polakoski allowed us to ask whether the MHS-10 monoclonal antibody would cross react with these previously described acrosomal matrix constituents. As seen in FIG. 6, the single bands of purified sperminogen and acrosin lanes 3+4 Were unreactive with the MHS-10 monoclonal antibody, although the boar sperm extract (lane 2B) clearly contained immunoreactive proteins. In addition, the purified preparation of acrosin possessed a considerably higher apparent molecular weight than SP-10. Although the purified preparation of sperminogen was of similar apparent molecular weight as a major immunoreactive peptide of SP-10 at 29 kD, the MHS-10 monoclonal antibody did not recognize the sperminogen protein band on the Western blot.

Figure 7:
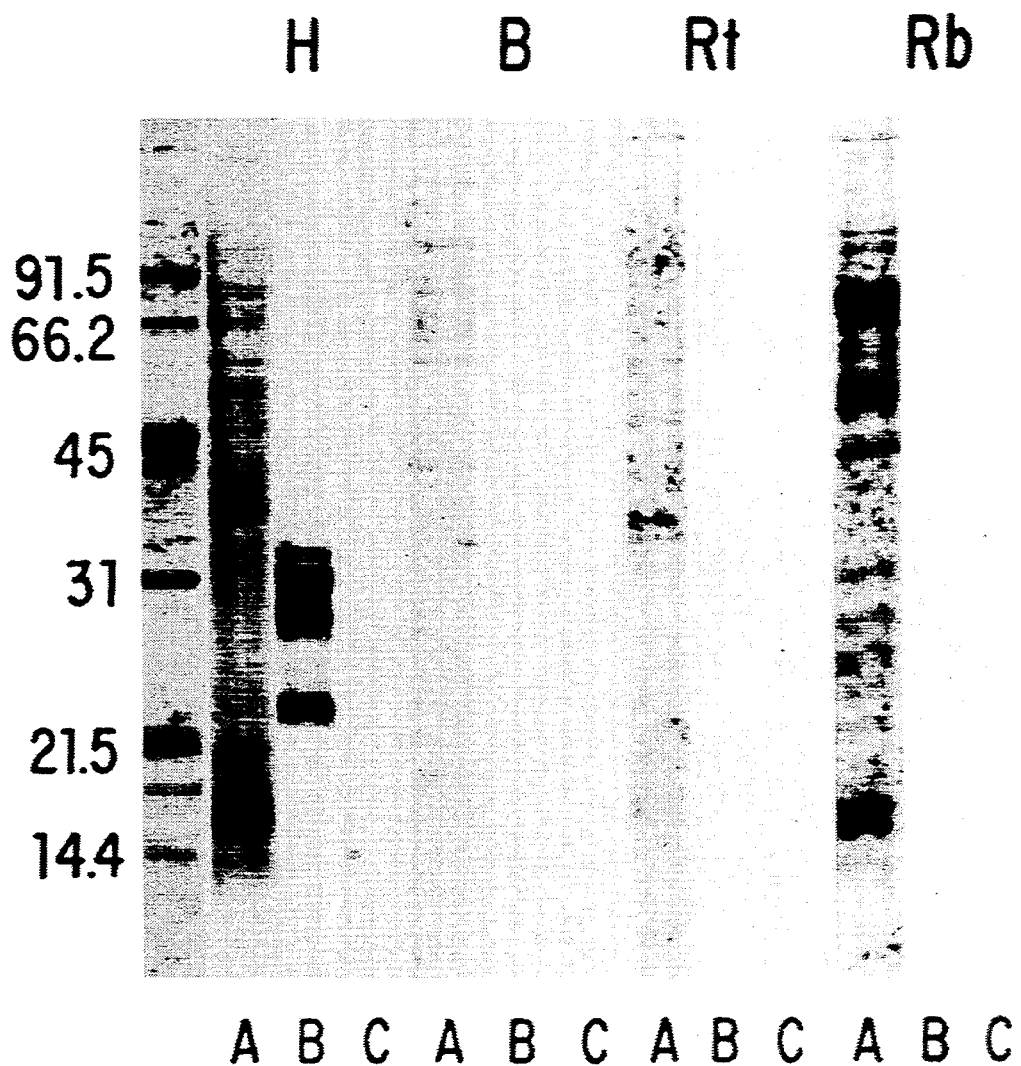
FIG. 7. Immunoblot (minigels) of human (H), bull (B), rat (Rt) and rabbit (Rb) sperm extracted with 1% SDS. Each lane was loaded with 3 ug of protein which was separated by SDS-PAGE and transferred to nitrocellulose. Lanes were stained with Amido Black (lanes A), a 1:2000 dilution of MHS-10 Mab ascites (lanes B), or a 1:2000 dilution of null ascites (lanes C). Lanes incubated with ascites were subsequently incubated with HRPlabelled goat anti-mouse IgG secondary antibody followed by 0.05% DAB and hydrogen peroxide. The left lane contained molecular weight standards of the indicated molecular weights.

Western blotting of sperm extracts of several species, including the bull, rat, and-rabbit failed to demonstrate the presence of proteins which immunoreacted with monoclonal antibody MHS-10 (FIG. 7). In addition to the species shown on in FIG. 7, guinea pig and cat sperm extracts were observed to lack reactivity with the MHS-10 monoclonal antibody on Western blots.

Figure 8:
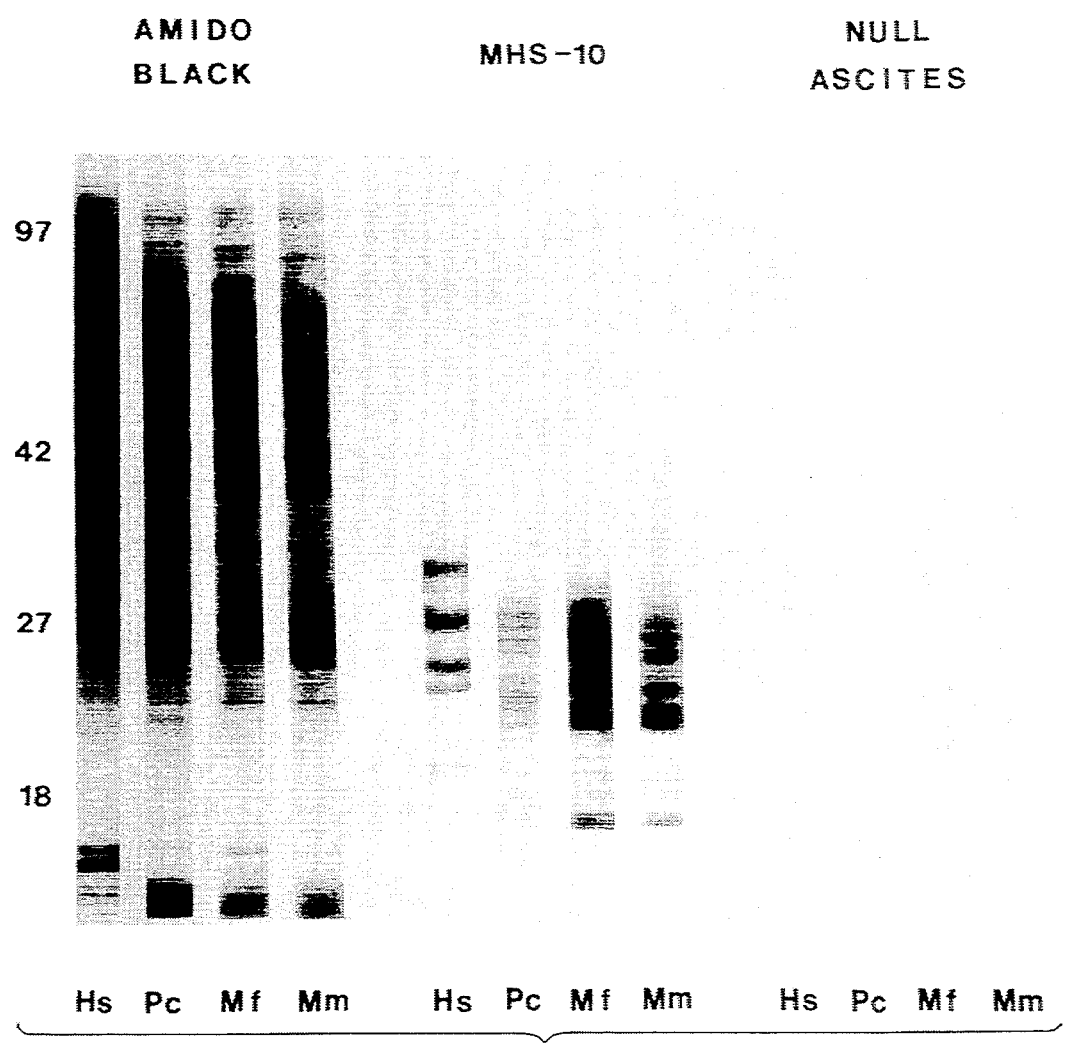
FIG. 8. Immunoblot of human (Hs), *Papio cynocephalus* (Pc), *Macaca mulatta* (Mm), and *Macaca fascicularis* (Mf) sperm extracted with 1% SDS. Each lane was loaded with 10 ug of protein which was separated by SDS-PAGE and transferred to nitrocellulose. Lanes were stained with Amido Black, a 1:2000 dilution of MHS-10 ascites, or a 1:2000 dilution of null ascites as indicated. Lanes incubated with ascites were subsequently incubated with HRP-labelled goat anti-mouse IgG secondary antibody followed by 0.05% DAB and hydrogen peroxide.

Peptides immunoreactive with the MHS-10 monoclonal antibody were detected on Western blots containing sperm extracts of *Papio cynocephalus anubis, Macaca mulatta,* and *Macaca fascicularis* (FIG. 8). Each of these primates showed a polymorphic pattern of immunoreactivity similar to the poylmorphic pattern of immunoreactivity observed on extracts of human sperm. However, sperm extracts from each of these primates showed immunoreactive peptides of lower apparent mass than in the human sperm extracts, including a band at approximately 14 kDa.

Figure 9:
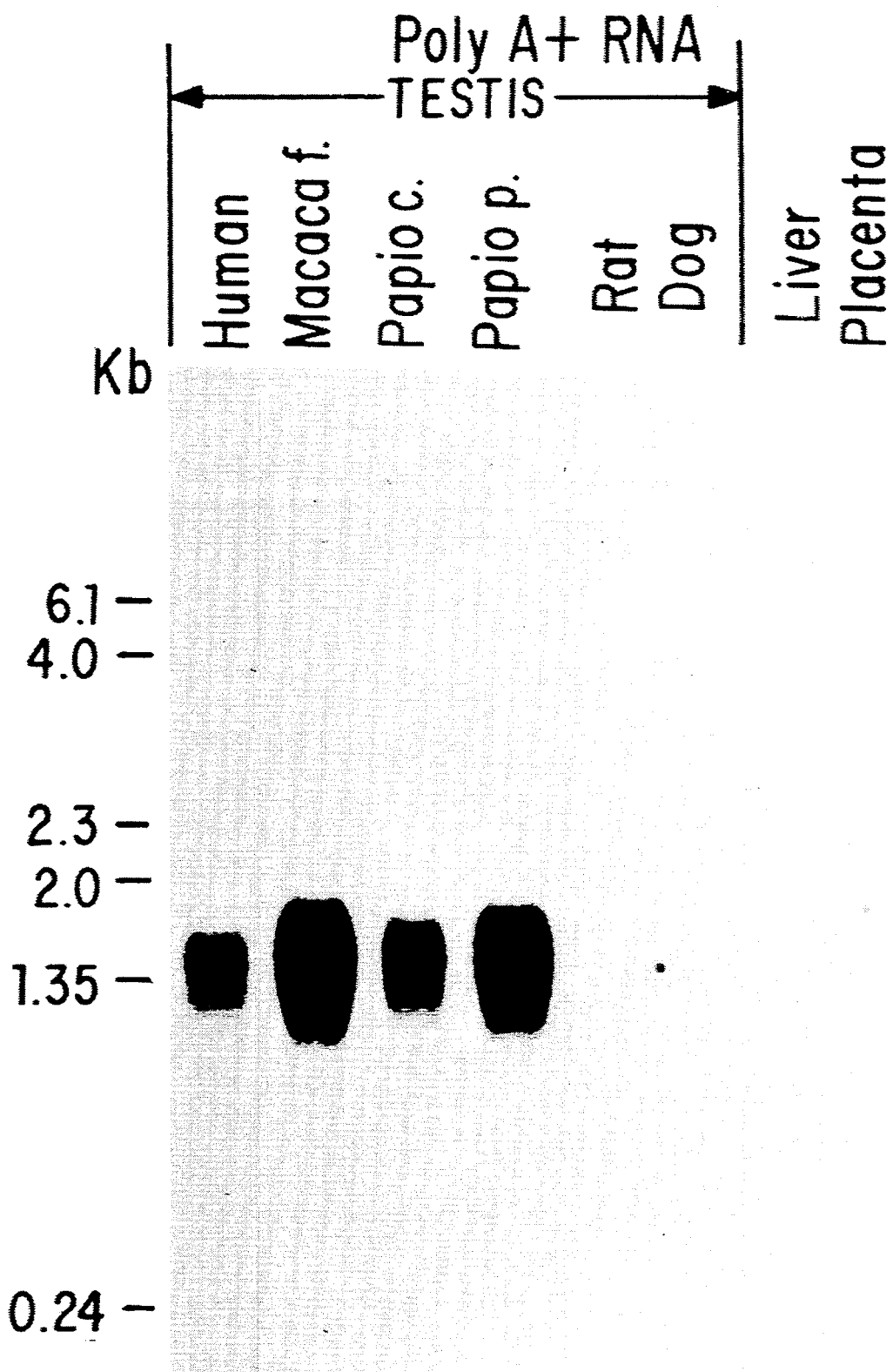
FIG. 9. Northern blot of poly A+RNA isolated from testes of human, baboon (*Papio papio, Papio cyngcephalus anubis*), rhesus (*Macaca fascicularis*), dog, and cat as well as human placenta and liver. The blot was hybridized with a $p^{32}$ labelled probe spanning 628 bp of the open reading frame for human SP-10. A 1.35 kb mRNA is observed in lanes containing human, baboon, and rhesus poly A+testis RNA.

Northern blots (FIG. 9) which were loaded with poly A+RNA purified from testes of *Papio papio, Papio cynocephalus anubis,* and *MaCaca fascicularis,* demonstrated that these species testes contained a 1.35 kb mRNA which hybridized with the 628 bp SP-10 probe. This 1.35 kb mRNA was of similar size to human testicular mRNA (FIG. 9). Poly A+RNA from dog and cat testes did not hybridize with the probe nor did poly A+RNA obtained from human placenta or liver (FIG. 9).

Discussion

The identification of peptides in pig sperm extracts which were immunoreactive with the MHS-10 monoclonal antibody and were of similar apparent molecular weight to human SP-10 indicates that pig sperm contains SP-10. The lack of immunoreactivity of purified preparations of acrosin or sperminogen with the MHS-10 monoclonal antibody, despite the fact that the pig sperm extract was immunoreactive, indicates a dissimilarity between SP-10 and these previously described intra-acrosomal components. This suggests that the SP-10 protein is a novel intra-acrosomal constituent.

The polymorphic pattern of SP-10 peptides observed on Western blots of human sperm extracts was also observed on sperm peptides obtained from baboon and rhesus. Why these multiple immunoreactive peptides of varying mass appear in human and the other primate sperm has not been determined. Because the MHS-10 monoclonal antibody was successfully employed to screen a lambda gt11 expression library for SP-10, it is likely that the MHS-10 epitope is proteinaceous rather than a carbohydrate. The open reading frame for human SP-10 predicts a protein of 265 amino acids with a mass of 28.3 kDA. See Example 9. Since two canonical N-linked glycosylation sites were identified on human SP-10, it is likely that the forms of SP10 with apparent molecular weight above 28.3 kDa represent glycosylated SP-10. Each of the Western blots of primate sperm showed immunoreactive bands in the upper range of the pattern at approximately 29 kDa. These bands are of approximately the mass predicted from the nucleotide sequence without any glycosylation. Like the human sperm extracts, multiple immunoreactive forms below 29 kDa were observed in the other primates. This similarity between human, baboon, and macaque SP-10 suggests that the mechanisms responsible for generation of the polymorphism of SP-10, be they proteolysis, post-translational modification, multiple gene products, or a combination of these causes, are operating in baboon and macaque sperm as well as human sperm.

Pig SP-10, on the other hand, did not demonstrate the multiple immunoreactive peptides below 29 kDA seen with the extracts of primate sperm. Like the human SP-10, pig sperm immunoblots showed a band at approximately 34 kDa as well as a major immunoreactive band at approximately 29 kDa, (approximately the 28.3 kDa mass for the protein predicted from the nucleotide sequence). It is unclear at present whether this heterogeneity reflects differences in amino acid sequence, post-translational modification, or results from variation in viability and proteolysis of the sperm preparations.

Because SP-10 remained associated with the sperm head following ionophore induced acrosome reaction and evidence has been presented that the MHS-10 monoclonal antibody inhibited sperm/egg interaction in the hamster egg penetration test, it is possible that SP10 may be an effective immunogen for inducing antibodies which would interdict fertilization in vivo, provided that sufficient levels of antibody are induced within the oviduct. The observation that a 1.35 kb mRNA for SP-10 is common to baboons, macaques, and humans provides additional evidence supporting the similarities observed between humans, baboons, and macaques in immunoreactive SP-10 observed on Western blots. Together these data indicate that macaques and baboons may be appropriate primate models for testing the anti-fertility potential of a recombinant SP-10 vaccine.

In summary, in the present study, a monoclonal antibody to SP-10 (MHS-10) was employed on Western blots to identify immunoreactive SP-10 in sperm extracts from baboon (*Papio cynocephalus anubis*) and two macaques (*Macaca mulatta* and *Macaca fascicularis*). In each of these primates, the MHS-10 monoclonal antibody recognized a polymorphic pattern of immunoreactive peptides similar to the human pattern. Immunoreactive SP-10 was also demonstrated in pig sperm. Using purified preparations of the previously described intra-acrosomal molecules acrosin and sperminogen in the pig, we observed that the MHS-10 monoclonal antibody did not react with these proteins, indicating SP-10 is distinct from these known acrosomal components. Sperm from several common species, including the rabbit, bull, rat, guinea pig and cat, did not immunoreact with the MHS-10 monoclonal antibody. Utilizing a radioactive probe spanning 628 nucleotides of the open reading frame for SP-10 on Northern blots of poly A+ RNA obtained from testes of *Macaca fascicularis, Papio papio,* and *Papio cynocephalus anubis,* a 1.35 kb messenger RNA of identical size to the mRNA from human testes was identified. These results indicate that baboons, macaques, and pigs may be appropriate models for testing of an SP-10 based contraceptive vaccine.

EXAMPLE 9

Cloning and Sequencing of cDNAs Coding for the Human Intra-Acrosomal Antigen SP-10

This example describes the characterization of cDNAs coding for the human sperm acrosomal protein, SP-10. cDNAs coding for SP-10 were isolated, sequenced, and the deduced SP-10 amino acid sequence was analyzed. This work identified some fundamental characteristics of the SP-10 protein and suggests that alternative splicing of the SP-10 mRNA occurs. Using the SP-10 cDNAs and the MHS-10 monoclonal antibody, it will be possible to study the expression of SP-10 during spermatogenesis at both the transcriptional and post-transcriptional levels. Overexpression of SP-10 using the SP-10 cDNAs should also allow us to assess its value as a contraceptive vaccine immunogen. Assessing immunogenicity of several SP-10 peptides using recombinant methods is also made possible by having cloned and sequenced the SP-10 cDNAs.

Materials and Methods

1. Isolation and Analysis of cDNA Clones

The MHS-10 monoclonal antibody was used to probe a human testis lambda gt11 expression library. The library was a gift from Jose Millan. See Millan et al., *Proc. Natl. Acad. Sci. USA,* 84:5311–15 (1987), incorporated herein by reference. The library was plated at a density of $5 \times 10^4$ plaque-forming units per 150 mm Petri dish with E. coli Y1090 as host bacterium. After growth at 42° C. and induction with isopropyl-B-D thiogalactoside, the nitrocellulose filters were preincubated with 5% milk and 5% goat serum and screened with a 1:1000 dilution of MHS-10 monoclonal antibody (isotype IgG1). Bound MHS-10 was detected by use of a goat anti-mouse IgG coupled to horseradish peroxidase (Jackson ImmunoResearch Laboratories). A putative clone was identified upon screening 50,000 pfu from the expression library. This phage was plaque purified using MHS-10 and showed no reactivity to other IgG1 monoclonals or to the goat anti-mouse IgG. This clone contained a cDNA insert of 214 base pairs (bp), designated SP-10-214, which was nicktranslated (Bethesda Research Labs) with p$^{32}$ dCTP (ICN) and used to reprobe the gt11 library to identify additional clones using the procedure of Benton and Davis, Science, 196:180–182 (1977), incorporated herein by reference. Five additional clones were identified.

Three plaques homologous to the 214 bp clone were purified and the phage DNAs isolated. These phage DNAs were digested with EcoR1 and run on a 1% agarose gel. The EcoR1 digestion produced cDNA insert bands of approximately 650 bp and 400 bp for all three isolates. Northern blots performed using either the 650 bp or the 400 bp insert of cDNA SP-10-5 as a probe gave identical results (data not shown). The 650 bp and 400 bp inserts for all three phage isolates were isolated and subcloned into pGEM3Zf (ProMega). The cDNA designated SP-10-5 is a composite of the cDNA inserts contained in the plasmids pGEM-SP-5-650 and pGEM-SP5-400. The cDNAs designated SP-10-8 and SP-10-10 are also composites of their respective 650 bp and 400 bp cDNAs fragments. Nested deletions were made from each end of the cDNA fragment in pGEM-SP-5-650 and pGEM-SP-5-400 using the Erase-a-Base System (ProMega), and both strands of each insert were sequenced using a Sequenase sequencing kit (US Biochemicals). Nested deletions were made from one end of the 650 bp SP-10-10 cDNA fragment in pGEM-SP-10-650 and one strand was sequenced. The 400 bp SP-10-10 fragment in pGEM-SP-10-650 was sequenced by priming from both ends. The entire open reading frame for SP-10 is a composite constructed from the SP-10-5 and SP-10-10 cDNAs.

2. Homology Analysis

Homology searches of the Genbank, National Biomedical Research Foundation (NBRF) protein and Swiss Protein Library databases were performed using the Pearson and Lipman FASTA and LFASTA programs. See Pearson and Lipman, Proc. Natl. Acad. Sci. USA, 85:2444–48 (1988), incorporated herein by reference. Comparisons were run with ktups of 1 and 2.

3. RNA Isolation and Northern Blots

Human testes were obtained from elective orchiectomies for prostate carcinoma from patients untreated with steroids and frozen in liquid nitrogen. The tissue was then ground to a powder on dry ice and the RNA isolated using guanidine isothiocyanate followed by CsCl centrifugation. Chirgwin et al., Biochemistry, 18:5294–99 (1979), incorporated herein by reference. Poly(A)+RNA was isolated using oligo(dT)-cellulose (Collaborative Research) as described by Bantle et al., Anal. Biochem., 72:413–427 (1976), incorporated herein by reference.

One microgram of human testes poly (A)+ RNA and 2 μg of human placental and liver poly (A)+ RNAs were electrophoresed on a 1% formaldehyde-agarose gel. See Lehrach et al., Biochem., 16:4743–51 (1977), and Goldberg, Proc. Natl. Acad. Sci. USA, 77:5794–98 (1980), both of which are incorporated herein by reference. The RNA was blotted to Biotrace membrane (Gelman), and its integrity was judged by backshadowing the 18S and 28S ribosomal RNA bands with U.V. light. The membranes were prehybridized (50% formamide, 1% milk, 5 X SSPE, 1% SDS and 100 μg/ml salmon sperm DNA) and then hybridized with a p$^{32}$ labelled 634 bp fragment containing part of the coding region from SP-10-5 (bps 67–695). Final membrane washes consisted of 0.2X SSPE, 0.5% SDS at 65° C.

Results

1. Characterization of the SP-10 cDNAs

Figure 10:
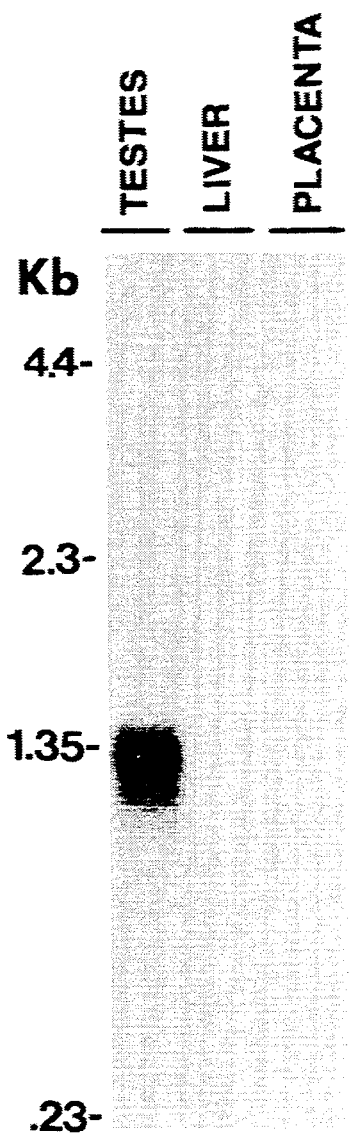
FIG. 10. Northern blot analysis of poly(A)+RNA from human testes, liver, and placenta. One ug of testes poly(A)+RNA, and 2 ug of liver and placental poly(A)+RNAs were electrophoresed on a 1% formaldehyde agarose gel, transferred to Biotrace membrane and probed with a nick translated 634bp SP-10-5 fragment. The SP-10 mRNA is approximately 1.35 kb in length.

A human testis cDNA expression library was screened using the MHS-10 monoclonal antibody. The cDNA insert of one MHS-10 reactive plaque was purified, sequenced, and found to be 214 bp in length. This insert was then used as a probe to isolate 3 larger cDNAs designated as SP-10-5, SP-10-8, and SP-10-10. A 634 bp fragment of cDNA SP-10-5 was used to probe northern blots containing poly (A)+ RNA from human testes, liver, and placenta (FIG. 10). One band at 1.35kb was present in the testes RNA but not in either the liver or placental RNA lanes.

Sequence analysis revealed that cDNAs SP-10-5 and SP-10-10 overlapped extensively (FIG. 11A). By combining the sequences for SP-10-5 and SP-10-10, a partial cDNA of 1117bp with an open reading frame of 795 bases, 265 amino acids, was identified for the SP-10 protein. With the exception of an in-frame deletion of 57 bp (19 amino acids) in SP-10-10, the remaining overlapping sequences for SP-10-5 and SP-10-10 were identical. The 5' and 3' ends of the SP-10-8 sequence were identical to the SP-10-5 and SP10-10 cDNA sequences where they overlapped, but like SP-10-5 did not have the 57 bp deletion present in the SP-10-10 sequence.

The sequence analysis also identified a consensus polyadenylation sequence at position 1094, 236 bp 3' of the TAG termination codon, and a putative eukaryotic mRNA degradation sequence 71 bp 3' of the stop codon. The 5' sequence (CCAG) that flanked the initiator methionine was similar to a consensus sequence found 5' to most eukaryotic start codons.

The amino acid sequence for SP-10 deduced from the cDNA sequence predicted a protein of 28.3 kD. Three different repeating amino acid motifs were identified (FIG. 11A and FIG. B). The first motif (Ser, Gly, Glu, Gln, (Pro or Ala)) occurred 7 times. There were two additional variants of the first repeat, (Val, Gly, Glu, Gln, Pro) and (Ser, Asp, Glu, Gln, Pro) which differed by only one amino acid. The second motif (Ser, Glu, His, (Gly or Ala), Ser) was repeated 3 times, while the third motif (Ser, Gly, Glu, His) was repeated 4 times. These three motifs comprised 76 of the 108 amino acids between amino acids 66 and 174.

A hydrophobicity plot of the SP-10 amino acid sequence (FIG. 11C) showed a hydrophobic amino terminus characteristic of a signal peptide. The central portion of the protein that contained the repeated motifs had several hydrophilic domains while the carboxy terminus was quite hydrophobic. Two canonical N-linked glycosylation sequences (Asp-X-Ser(Thr)) existed at amino acids 48 and 258, while a stretch of serines and threonines that began at amino acid 80 suggested possible O-linked glycosylation sites. The sequence, (Ser-(Asp or Glu)-X-X-Pro), which occurred at residue 140, has also been suggested as a possible target site for O-linked glycosylation (Gerry Hart, personal communication).

2. Homology Searches

The entire SP-10 cDNA and amino acid sequences were compared to the Genbank, NBRF, and Swiss sequence banks using the library search programs Fasta and tFasta at ktups of both 1 and 2. Neither the SP-10 nucleic acid or amino acid sequences showed any homology with the sequences in the banks. The 3 repeated amino acid motifs were also compared to the same sequence banks. While several proteins contained a single copy of one motif, none contained multiple copies of any motif.

Discussion

We have described the cloning and initial characterization of cDNAs coding for the human sperm acrosomal protein SP-10. Sequence analysis of the SP-10 cDNAs revealed several interesting features of the SP-10 protein. A hydrophobicity plot generated from the deduced amino acid sequence showed SP-10 contained a strongly hydrophobic amino terminus characteristic of a signal peptide. Furthermore, when the amino terminal 20 amino acids were analyzed individually for charge and hydrophobicity, they conformed well to the characteristics of a signal peptide. A signal peptide would be required to transport the SP-10 protein through the membrane of the endoplasmic reticulum and into the Golgi vesicles that coalesce to form the developing acrosome.

Following the signal sequence, a central peptide core exists containing several hydrophilic domains comprised almost entirely of the three repeating peptide motifs. It should be noted that because of the 19 amino acid deletion, cDNA SP-10-10 is missing a single copy of two of the motifs. The role these unique repeats play in the functioning of SP-10 is still unclear since no proteins were found in the Genbank, NBRF, and Swiss sequence banks that contained multiple copies of the motifs.

Analysis of the cDNA sequences revealed 2 potential N-linked glycosylation sites and possible O-linked glycosylation sites. Carbohydrates at these positions could account for the difference in size between the 34 kd SP-10 species observed in Western blots and the 28.3 kd peptide (26 kd after removal of the signal peptide) calculated from the deduced amino acid sequence. This size discrepancy was expected, since other acrosomal proteins have been shown to be glycosylated, including acrosin of the rabbit, boar, and goat. Human and boar proacrosin, for example, migrated at approximately 55 kd by SDS PAGE but were synthesized from mRNAs that coded for peptides of only about 45 kd.

Figure 12:
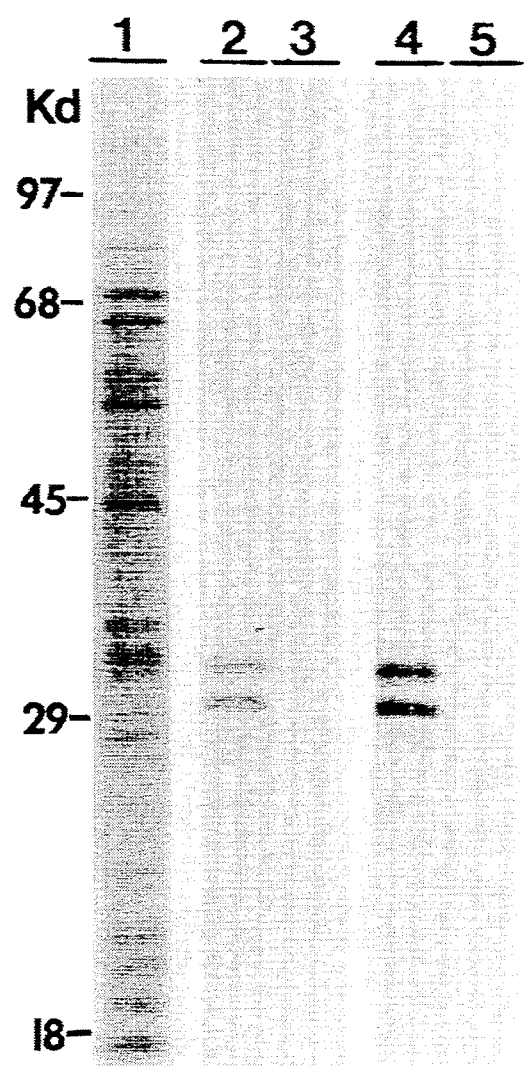
FIG. 12. Western blot analysis of human sperm extracts using the monoclonal antibody MHS-10 and the SP-10 polyclonal antiserum generated toward recombinant fusion protein, pWRSP-210. MHS-10 and the polyclonal antiserum recognized an identical set of SP-10 polypeptides in sperm extracts. Human sperm extracts were prepared and subjected to SDS PAGE, blotted, and incubated with the monoclonal and polyclonal antibodies as described in Materials and Methods. Amido black staining of the electrophoresed sperm extracts, lane 1. Extracts incubated with MHS-10, lane 2, or null ascities lane 3. Extracts incubated with the SP-10 polyclonal antiserum, lane 4, or preimmune serum, lane 5.

The size heterogeneity previously observed for the SP-10 protein is apparent in FIG. 12. Differing degrees of glycosylation could account for some of the heterogeneity on Western blots. The internal deletion within the SP-10-10 cDNA suggested that differential splicing of the SP-10 transcript might also account for some of the heterogeneity. The SP-10-10 mRNA with a 19 amino acid deletion would code for a protein 2 kd smaller than that produced by the SP-10-5 mRNA. However, it is unlikely that alternative splicing was the major cause of the heterogeneity, since the SP-10 transcript was a relatively discrete band on Northern blots. Proteolysis of the SP-10 protein during sperm maturation and storage probably also contributed to its size heterogeneity. The fact that all three SP-10 cDNAs isolated to date shared identical 3' untranslated sequences where they overlapped suggested that multiple SP-10 genomic genes were probably not responsible for the heterogeneity.

Figure 11C:
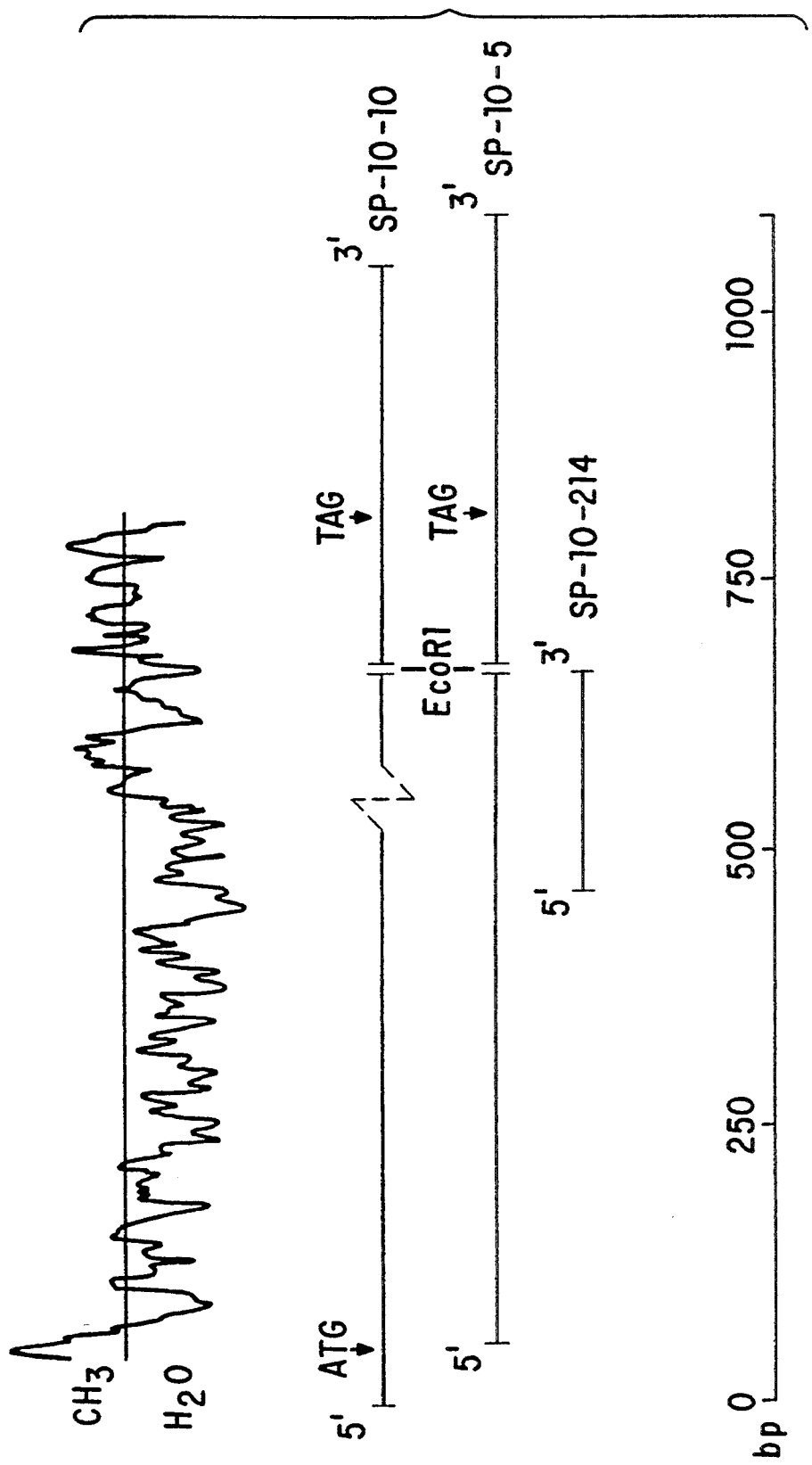
Fig. 11C. Hydrophobicity plot generated from the deduced SP-10-5 amino acid sequence. Hydrophobic residues lie above the center line and hydrophilic residues lie below the line. The SP-10-5, SP-10-10, and SP-10-214 cDNAs are indicated below the the plot. The internal EcoR1 site at bp 695 is indicated.

The production of a MHS-10 immunoreactive fusion protein from the original 214 bp cDNA has localized the MHS-10 epitope to a 71 amino acid peptide of the SP-10 protein. The amino terminal 34 amino acids of this 71 amino acid peptide were comprised entirely of two of the three types of hydrophilic motifs, while the carboxy terminal 37 amino acids were quite hydrophobic (FIG. 11C). Since MHS-10 was very likely generated to a hydrophilic region of the SP-10 peptide, one or more of the motifs in this 34 amino acid stretch probably comprises or contributes to the MHS-10 epitope.

The availability of the cDNAs has allowed us to generate large amounts of SP-10 as a fusion protein. The recombinant antigen will allow us to test two hypotheses: 1) that SP-10 may be effective as a contraceptive vaccine immunogen; and 2) that sera from persons with anti-sperm antibodies may recognize recombinant SP-10. If the latter proves to be the case, immobilized recombinant SP-10 may serve as a useful target antigen for measuring anti-sperm antibodies.

In summary, cDNAs coding for the intra-acrosomal protein SP-10 were cloned and characterized as a first step in understanding the expression of this antigen during spermatogenesis. Three overlapping SP-10 specific cDNAs were isolated from a human testes cDNA expression library. These cDNAs hybridized to a 1.35kb mRNA which was present in human testes but was not found in liver or placenta. Complete sequencing of these cDNAs, designated SP-10-5, SP-10-8, and SP-10-10, produced an 1117 bp sequence containing a 265 amino acid coding region for the SP-10 protein. Hydrophobicity plots generated from the deduced amino acid sequence showed a very hydrophobic amino terminus characteristic of a signal peptide. Sequence data showed that three different amino acid repeats occurred a total of 16 times in the central third of the SP-10 protein. Interestingly, cDNA SP-10-10 has a internal 57bp (19aa) in-frame deletion which is not present in SP-10-5, suggesting that alternative splicing generates more than one SP-10 mRNA. The SP-10 protein appears to be a unique acrosomal protein based on previous immunohistological data and on the observation that SP-10 cDNA sequences did not show any significant homology to other sequences found in the Genbank, NBRF, or Swiss sequence banks.

EXAMPLE 10

Preparation of Antigen by Transformed Microorganisms

The SP-10-5A cDNA insert will be excised from pGE-SP-10-5 with KPN I and SST I. The ends will be blunted using Mung Bean Nuclease and NcoI linkers attached with T4 DNA ligase. (The SP10-5 cDNA contains no internal NcoI sites.) The linkers will then be cleaved with NcoI and the cDNA separated from unligated linkers by agarose gel electrophoresis and electroelution of the fragment. The cDNA will then be ligated into the NcoI site of the E. coli expression vector pKK233-2 (Pharmacia). This vector contains an IPTG (isopropyl-B-D-thiogalacto-pyranoside, U.S. Biochemicals Corp.) inducible promotor and the lacZ ribosome binding site 5' to the cDNA insertion site and a consensus transcription termination sequence 3' to the cDNA insertion site. The linkers ligated to the cDNA will be a mixture of 3 NcoI linkers, each containing an AUG start codon in one of the three reading frames. The cDNAs ligated into pKK233-2 will be transformed into E coli. The resulting colonies will be transferred to nitrocellulose and the filter placed onto an agar plate containing 2mM IPTG for 4 hrs at 37° C. to induce production of the SP-10-5A protein. The filter is then incubated at 100° C. in 5% sodium dodecyl sulfate (SDS), dried, and incubated with MHS-10 MAB and horseradish peroxidase-labeled goat anti-mouse antisera. Colonies showing a positive reaction with the SP-10 MAB will be isolated and 1 ml overnight cultures grown in the presence of 2 mM IPIG. The recombinant E. coli will be collected by centrifugation and lysed in 4X protein loading buffer (4% SDS, 20mM TRIS (pH 8.0), 0.5 M 2-mercaptoethanol, 20% glycerol). These samples will be boiled, subjected to 1D SDS PAGE according to Laemli, Nature (Lond) 227:680 (1970), incorporated herein by reference, and Western blotted with the MHS-10 MAB and horseradish peroxidase labeled goat anti-mouse antisera. Those colonies showing an MHS-10 reactive band of approximately 27 kD (SP-10-5 cDNA codes for 266 amino acids) will be used to start large cultures for isolation of the recombinant SP-10-5 protein. Recombinant E. coli collected from the large preps will be lysed to release the SP-10-5 protein. After centrifugation to remove the cellular debris, the SP-10-5 protein will be purified using ion-exchange chromatography, MHS-10 MAB affinity chromatography, and preparative electrophoresis.

Expression in pGEX.

The pGEX system produces a "pure" (non-fusion) recombinant protein which we intend to use as a vaccine immunogen both alone and as a conjugate with other proteins which enhance the immune system. We have re-engineered the SP-10-5 cDNA SP-10-5 into the plasmid expression vectors pGEX -2T and pGEX-3X. Smith and Johnson, Gene 67:31-40 (1988), incorporated herein by reference. We have observed overexpression of recombinant SP-10. These constructs give a fusion polypeptide with the carboxyl terminus of the Schistosoma japonicum glutathione S- transferase protein. Smith et al., PNAS 83:8703-8707 (1986), incorporated herein by reference. Most fusion proteins produced in this system are soluble in aqueous solutions and can be purified from crude bacterial lysates under non denaturing conditions by affinity chromatography on immobilized glutathion. Using batch wash procedures several fusion proteins can be purified in parallel in under two hours with yields of up to 15 mg protein/liter of culture. Pure SP-10 is prepared by cleavage from the glutathione S-transferase carrier by digestion with site specific proteases such as thrombin (for pGEX-2T) and blood coagulation factor $X_a$ (for pGEX-3X). After digestion, the carrier and any uncleaved fusion protein are removed by absorption on glutathione agarose.

EXAMPLE 11

Testing Prototype Recombinant Vaccine for Immunogenicity in Rabbits

-Materials and Methods

1. Generation of SP-10 Rabbit Polyclonal Antisera

A 634 bp SP-10-5 EcoR1 fragment (bps 67-701, 202aa) and the original 214 bp SP-10 cDNA (bps 487-701, 71aa) that had EcoR1 ends were inserted into the E. coli expression vectors pWR590 and pWR591 respectively. See Guo et al., GENE, 29:251-254 (1984), incorporated herein by reference. The SP-10/B-galactosidase fusion protein that resulted from the 634 bp insertion was isolated according to Guo et al. and subjected to SDS PAGE. The SP-10/B-galactosidase fusion protein band was excised from the gel, frozen, ground to a powder, and resuspended in PBS.

Two rabbits were injected subcutaneously with equal volumes of the gel slurry and Freund's Complete Adjuvant (Gibco) and then were injected twice more with the gel slurry in Freund's Incomplete Adjuvant at two week intervals. Rabbits were bled, and the blood was processed for IgG using ammonium sulfate preciptation.

2. Western Blots and Immunofluorescence with Polyclonal Antisera Generated to a Prototype Recombinant Vaccine Donor sperm were washed in Ham's F-10 medium and frozen at −80° C. in water. After being thawed and vortexed, the sample was centrifuged at 10,000×g for 30 seconds, and one part supernatant was added to one part 2X Laemmli buffer (Laemmli, op. cit.) with B-mercaptoethanol. The proteins were subjected to SDS PAGE, transferred to nitrocellulose (Towbin et al., op. cit.), blocked in 5% milk in PBS/0.5% Tween-20, and incubated in a 1:1000 dilution of MHS-10, null ascities, SP-10 rabbit polyclonal, or rabbit preimmune sera in PBS/0.5% Tween 20, 1% milk for 2 hrs at room temperature. Goat anti-mouse (Jackson ImmunoResearch Labs) or goat anti-rabbit (HyClone) IgG-horseradish peroxidase was used at 1:5000 dilution, and reaction product was developed with 0.05% diaminobenzidine with 0.015% hydrogen peroxide. All washes between antibody incubations were done with PBS/Tween/1% milk.

For immunofluoresence studies, sperm were washed as described above, resuspended in PBS, and air dryed on slides. The slides were submerged in 3% paraformaldehyde for 30 min and methanol for 20 min to fix and permeabilize the sperm. They were preincubated in 10% goat serum in PBS for 15 min, and then incubated in monoclonal antibody MHS10, null ascities, rabbit SP10 polyclonal antisera, or rabbit preimmune antisera at a 1:500 dilution for 1 hr at room temperature in a humidity chamber. The slides were washed 5x in PBS and incubated in fluorescein labelled goat anti-mouse antisera (Jackson ImmunoResearch) (for MHS-10 and null ascities) or fluorescein labelled goat anti-rabbit antisera (HyClone) (for SP-10 polyclonal antisera and preimmune antisera) at 1:500 dilutions at room temperature for 1 hr in a humidity chamber. The slides were then washed 5x in PBS, mounted with 90% glycerol in 25mM Tris (pH 8.0) and viewed under a Zeiss phase microscope equipped with epifluoresence.

Results 1. western Blots and Immunofluorescent Localization

A 634 bp SP-10-5 fragment (bps 67-701, 202aa) and the original 214bp SP-10 cDNA (bps 487-701, 71aa) were inserted onto the E. coli expression vector pWR590 and expressed as B-galactosidase fusion proteins. The two constructs, identified as pWRSP-210 and pWRSP-71, produced fusion proteins that reacted specifically with MHS-10 on Western blots (data not shown). The pWRSP-210 fusion protein was used to generate polyclonal antisera in two rabbits. The antisera was used to probe Western blots containing SDS solubilized sperm extracts (FIG. 12). (The antisera produced by the two rabbits reacted identically on Western blots and in the immunofluorescent localization study; therefore only the data from rabbit #1 was shown here.) The polyclonal antisera reacted with the same series of bands (17–34 kd) on the human sperm extract lane as did the mAB MHS-10. No cross-reactivity was visible between the SP-10 polyclonal antisera and other non-SP-10 sperm proteins. The rabbit preimmune sera showed no reactivity with any sperm protein bands.

Paraformaldehyde fixed human sperm were reacted first with the SP-10 polyclonal antisera and then with a fluorescein labelled goat anti-rabbit secondary antibody. Only a cap on the head of the sperm, similar in morphology to the acrosome, showed any reactivity with the polyclonal antisera (FIG. 13A). This cap shaped immunofluorescent image was identical to that stained with monoclonal antibody MHS-10 (FIG. 13C). The preimmune antisera and null ascities showed no staining of the sperm at all (FIGS. 13B and 13D).

Discussion

The observations that the polyclonal antisera raised to the SP-10/β-galactosidase fusion protein: 1) reacted with the identical series of peptides on Western blots as did monoclonal antibody MHS-10 and; 2) showed precise immunofluorescent staining of the sperm acrosomal cap, provide two mutually supporting proofs that the isolated cDNAs code for the SP-10 protein. Had the SP-10 cDNAs coded for a non-SP-10 protein that only shared the MHS-10 epitope, the Western blot and immunofluorescence data would likely not have been identical for MHS-10 and the SP-10 polyclonal antisera. The innoculated rabbits showed no apparent ill effect of receiving the SP-10 recombinant vaccine. This suggests the recombinant vaccine may prove to be safe and efficacious. The fact that the recombinant vaccine evoked a polyclonal response which recognized the native SP-10 provides further proof that the recombinant vaccine will be efficacious.

A recombinant SP-10 fusion protein was produced in an *E. coli* expression vector and used to generate a polyclonal antisera. This antisera stained the acrosomal cap in-situ and reacted with a similar set of peptides on Western blots as did a monoclonal antibody to SP-10.

EXAMPLE 12

Chromosomal Location

Genomic blots containing mouse/human cell hybrid DNAs were hybridized with the 5' 634 bp portion of SP-10-5. Table I shows the hybrids positive when screened for the SP-10 gene and indicates which complement of chromosomes were contained in these hybrids.

This table is compiled from 33 cell hybrids involving 16 unrelated human cell lines and 4 mouse cell lines. See Shows, et al., *Advances in Human Genetics*, volume 12, Eds. H. Harris and K. Hirschhorn, (Plenum Press, New York and London), 1982, pp. 341–452; Shows, et al., *Somat. Cell Mol. Gen.*, 10:315–318 (1984); and Shows, et al., *Cytogenet. Cell Genet.* 21:99–104 (1978), all of which are incorporated herein by reference. The hybrids were characterized by karotypic analysis and by mapped enzyme markers. See Shows, TB. 1983, *Isozymes: Current Topics in Biological and Medical Research*, Volume 10, pp. 323–339, Eds. M. C. Rattazzi, J. G. Scandalios, and G. S. Whitt, Alan R. Liss, New York, incorporated herein by reference. The "t" in the table indicates a chromosome translocation for a particular chromosome, but no intact chromosome is present. (See under Translocations).

The DNA probe for the DNA probe SP-10 was hybridized to Southern Blots containing EcoRI digested DNA from the human-mouse hybrids listed in the table. The scoring for the probe SP-10 was determined by the presence (+) or absence (−) of human bands in the in the hybrids on the blots. Concordant hybrids have either retained of lost the human bands together with a specific human chromosome. Discordant hybrids have either retained the human bands, but not a specific chromosome or the reverse. Percent discordancy indicates the degree of discordant segregation for a marker and a chromosome. A 0% discordancy is the basis for chromosome assignment.

The DNA probe for SP-10 mapped to human chromosome 11 by somatic cell hybrids. The hybrid XER-7 with the 11/X translocation: 11p12 or 11p11->11gter::Xq11->Xqter and the hybrid EXR-5CSAZ with the X/11 translocation: Xpter->Xq22::11q13->11qter would localize the SP-10 to the P12->q13 region of human chromosome 11.

Chromosome 11 gave a concordancy of 31 and a discordancy of X. Chromosome 16 gave the next highest concordancy and discordancy figures of 23 and 13 respectively. This data indicates that the genomic gene for SP-10 is located on chromosome #11, probably in the area of the 11q2 band.

EXAMPLE 13

Differential Diagnosis of Immature Germ Cells in Semen Utilizing Monoclonal Antibody MHS-10

Human semen contains, in addition to spermatozoa, a population of round nucleated cells predominantly composed of germ cells, originating from the testis, and inflammatory cells (leukocytes). Although, in fertile individuals, round cells represent less than 5% of the total number of cells in semen, they are increased in cases of infertility associated with infection or hormonal alterations of normal spermatogenesis. Germ cells found in semen include spermatids and spermatocytes. The differentiation between the different stages of sperm precursors and leukocytes by light microscopy of semen smears using conventional staining techniques has been unreliable, due to morphological similarities in size, and requires a highly trained eye for accurate diagnosis. Round spermatids and spermatocytes could be mistaken for lymphocytes, while non-separated spermatids sharing a common cytoplasm could be mistaken for polymorphic nuclear leucocytes.

Anti-leukocyte monoclonal antibodies have recently been employed in immunocytochemical techniques to define leukocytes and their subpopulations in semen smears. Identification of sperm precursors using polyclonal antibodies raised against human germ cells and sperm has also been attempted using immunofluorescence assays followed by toluidine blue staining, but evaluation was difficult and necessitated the subsequent use of electron microscopy for positive identification. See Jassim and Festenstein, *J. Reprod. Immunol.*, 11:77 (1987), incorporated herein by reference.

This example shows a simple and reliable method for the differential analysis of immature germ cells in semen smears using a monoclonal antibody (mAb) probe, MHS-10 (IgG1). This antibody recognizes a human sperm protein, (SP-10), which has been immunocytochemically localized by electron microscopy to Golgi phase spermatids and all subsequent phases of spermigenesis.

In this example, the MHS-10 antibody was used to histochemically stain semen smears using a standard immunoperoxidase technique. To evaluate potential cross reactivity with leukocytes, anti-HLe-1 (a pan-antihuman leukocyte mAb probe) was also used. The results indicate that round cell populations staining with anti-SP-10 did not stain with anti-HLe1. Spermatids at varying stages of acrosome development could be detected by the anti-SP-10 monoclonal antibody. The use of this antibody probe also allows for the rapid identification of various types of morphologically abnormal germ cells in semen smears.

Materials and Methods

1. Semen samples

Semen samples were obtained from 34 subjects. Seven of these were from fertile men defined by having fathered at least one child and having no recent history of venereal infection. Three were from severely oligospermic patients ($<10\times10^\circ$ sperm/ml ejaculate). Five were from azoospermic patients. Eight were from polyspermic patients ($>250\times10^\circ$ sperm/ml ejaculate). Six were from patients defined as having increased round cells in their semen and five were from vasectomized patients. The infertile patients were from Brigham and Women's Hospital, Boston, Mass. Routine semen analysis was performed as described in Hill, et al., *Fertil. Steril.*, 47:460 (1987), incorporated herein by reference.

2. Preparation of semen smears

Liquefied semen was centrifuged at 600×g for 10 minutes. The seminal plasma was aspirated and the cellular pellet washed twice with phosphate buffered saline (PBS: O.01M, pH 7.2). The final pellet was resuspended in PBS to approximately $10^7$ cells/ml and 5 μl of this suspension was applied to each spot of 8-spot Teflon-coated microscope slides (Roboz Surgical, Washington, D.C.). The slides were dried and fixed in acetone for 10 minutes and frozen at −70° C.

3. Monoclonal antibodies

MHS-10 cell line (IgG$_1$) was subcloned two times and grown as ascites tumors. Balb/c mice (Charles River, Boston, Mass.) were primed with two i.p. injections of 0.5 ml sterile Pristane (2,6,10,14-tetramethylpentadecane: Sigma Chemical Co., St. Louis, Mo.) at 2-week intervals. One week following the second injection, $10^7$ hybridoma cells were injected i.p. in 0.5 ml serum-free, sterile RPMI-1640 medium (Gibco, Grand Island, N.Y.). The ascites fluid was collected and cleared of cellular debris by centrifugation (1,000×g) and stored at −60° C. until needed. Anti-HIe-1 was purchased from Becton Dickinson, Mountain View, Calif.

4. Immunohistologic staining of sperm and round cells

Semen smears were immunohistochemically stained using the Streptavidinbiotin-peroxidase system (SBP) (Histostain SP-kit, Zymed Laboratories South San Francisco, Calif.) as described in Wolf and Anderson, *Fertil. Steril.*, 49:497 (1988), incorporated herein by reference. After saturation of non-specific binding sites with non-immune rabbit serum for 10 minutes, 10μl of mAb was incubated on individual spots of the slides for 30 minutes at 37° C. Biotinylated secondary antibody was then added (10μl) for 10 minutes, followed by 10μl of streptavidin peroxidase conjugate for 5 minutes. Immunoreaction product was developed with the chromogen aminoethylcarbazole in the presence of the substrate hydrogen peroxide for 5 minutes at 37° C. The smears were counterstained with hematoxylin and mounted by a aqueous mounting medium.

Each specimen slide had one spot to which 10μl PBS was added, instead of primary antibody as control. In addition, they each had one spot to which MHS-10 ascites fluid (diluted 1/1000) was added, one spot to which anti-HLe-1 (diluted 1/20) was added, one spot to which a mixture of MHS-10 (diluted 1/250), and anti-HLe-1 (diluted 1/20) was added. All dilutions were made with PBS.

Evaluation of immunoperoxidase stained smears was made by Differential Interference Contrast microscopy using a Leitz 100/1.32 DIC objective on a Leitz Ortholux microscope equipped with a Leitz Vario Orthomat camera. Photographs were made with Ektachrome 160 Tungsten film.

Results

1. Immunostaining of semen smears

Figure 14A:
FIG. 14A. Cryostat section of human testis showing immunohistochemical spermatids and mature sperm (top righthand corner) (MHS-10, SBP, hematoxylin ×964).
Figure 14B:
FIG. 14B. Early stage spermatid in semen prior to acrosome formation. Note lack of immunostaining with MHS-10 (MHS-10, SPB, hematoxylin ×1600).
Figure 14C:
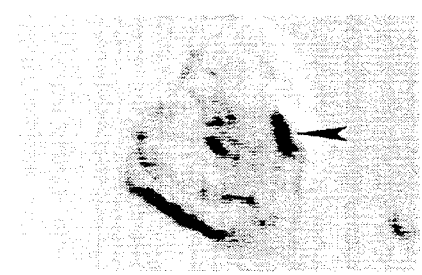
FIG. 14C. Golgi phase spermatid in semen smear. Note the oval shaped immunostaining acrosomal granule adjacent to the nucleus (arrow) (MHS-10, SPB hematoxylin, x2800).
Figure 14D:
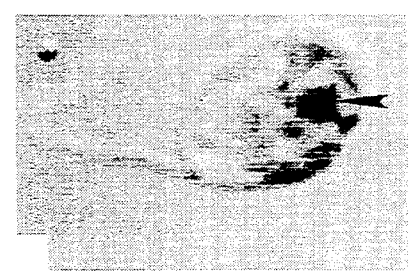
FIG. 14D. Late Golgi phase spermatid in semen smear showing immunostained acrosomal granule (arrow) and incomplete flagellum (MHS-10, SPB, hematoxylin x2600).

Within the semen smears, immature germ cells which had been sloughed at various stages of formation in the testis could be detected with the MHS-10 antibody probe to the intra-acrosomal antigen SP-10. Examples of MHS-10 positive germs cells are assembled according to stages of acrosome development (FIGS. 14B-F). FIG. 14B depicts an early stage spermatid prior to the onset of acrosome formation. FIG. 14C shows immunohistochemical staining of a developing spermatid containing an ovoid MHS-10 positive granule lying adjacent to the nucleus. This figure likely represents an early acrosomal granule in a Golgi phase spermatid. FIG. 14D shows a somewhat larger immunostained acrosomal granule in the Golgi phase of spermiogenesis as well as an incomplete flagellum.

Figure 14E:
FIG. 14E. Early cap phase spermatid in semen smear. Note uncondensed nucleus with immunohistostaining acrosome lying proximal to implantation fossa (MHS-10, SBp hematoxylin x2205).
Figure 14F:
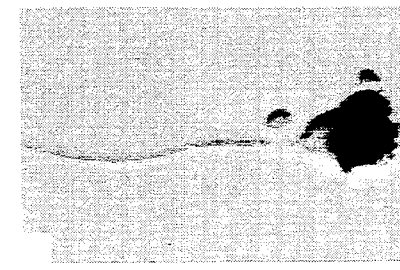
FIG. 14F. Mature sperm in semen smear showing a ccmplete immunohistostaining acrosome (MHS-10, SHP, hematoxylin x194B).

A spermatid displaying an uncondensed, open nucleus and an immunoreactive crescent is apparent in FIG. 14E. This represents a more advanced stage of acrosomogenesis, likely a cap phase spermatid. In this figure, the flattened acrosome is in a position proximal to the implantation site of the flagellum, a feature characteristic of early spermatid differentiation during which the flagellar anlage is implanted at the nucleus. Mature sperm, abundant in normal specimens (FIG. 14F) showed immunostained acrosomes, enveloping the condensed nucleus and in a position distal to the flagellum, typical of completed acrosomogenesis.

Figure 15A:
FIG. 15A. Immature germ cell in semen smear showing two nuclei within the same cytoplasm MHS-10, SBP, hematoxylin x2145).
Figure 15B:
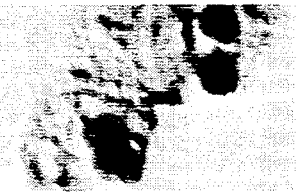
FIG. 15B. Spermatid in semen with two immunohistostained acrosomal granules within the same cytoplasm MHS-10, SBP, hematoxylin x2293).
Figure 15C:
FIG. 15C. Biflagellated sperm with two condensed nuclei (arrows) and completed acrosomes within the same cytoplasm. Note too, the sperm with a large uncondensed nucleus (lower left) and that with an abnormally large acrosome (lower right). (MHS-10, SBP, hematoxylin x1583).

Abberant germ cell morphologies indicative of defective cytokinesis were observed using the MHS-10 mAb. (FIGS. 15A-E). These included binucleated spermatids (FIG. 15A), spermatids containing two acrosomal granules within the same cell (FIG. 15B), and sperm containing two condensed nuclei enveloped by two acroscmes within a single sperm head (FIG. 15C arrows). Images such as those seen in FIGS. 15D-E were interpreted as representing intact intracellular bridges where daughter spermatids remained attached and were apparently sloughed off as a cohort of cells, displaying asynchronous development. Of the four attached cells seen in FIG. 15D, one germ cell was staged at the Golgi phase of spermiogenesis (arrows points to the acrosomal vesicle) and three others were staged at the Golgi phase of development.

Figure 15D:
FIG. 15D. Conjointed spermatids in semen smear displaying asynchormous development. Arrows point to acrosomal vesicles staged at Golgi phase (lower left hand corner) and to cap phase of formation, respectively (MHS-10, SBP, hematoxylin x1500).
Figure 15E:
FIG. 15E. conjoined spermatids in semen smear (MHS-10, SBP, hematoxyline x1854).
Figure 15F:
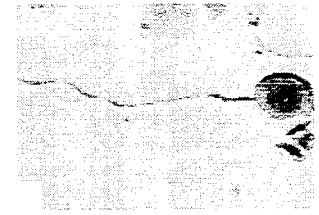
FIG. 15F. Biflagellated spermatids in semen smear showing immunoreactive cap phase acrosome and uncondensed nuclei (MHS-10, SBP, hematoxylin x1672).
Figure 15G:
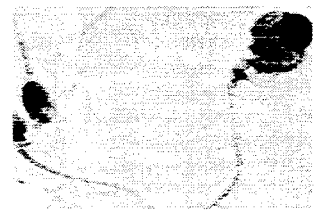
FIG. 15G. Sperm with uncondensed nuclei and microacrosome in semen smear. (MHS-10, SBP, hematoxylin x1967).
Figure 15H:
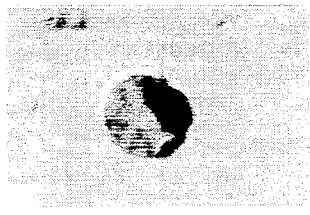
FIG. 15H. Cap phase spermatid lacking flagellum in semen smear (MHS-10, SBP, hematoxylin x2754).
Figure 15:
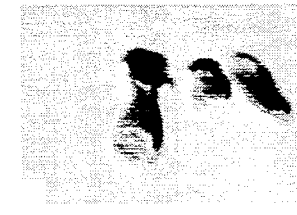
FIG. 15.

Other abnormal sperm phenotypes were also observed in semen stained using the monoclonal antibody MHS-10. Biflagellated tails were observed in germ cells showing immunoreactive cap phase acrosomes and uncondensed nuclei (FIG. 15F). Sperm displaying uncondensed nuclei with microacrosomes (FIG. 15G) as well as cap phase spermatids lacking flagella (FIG. 15H) were also observed.

Figure 15J:
FIG. 15J. Spermatid in semen smear showing a peripheral cuff of immunoreactive material (MHS-10, SBP, hematoxylin x2754).
Figure 15K:
FIG. 15K. Spermatid in semen smear showing a peripheral cuff or immunoreactive material (MHS-10, SBP, hematoxylin x2368).

In some cases, reactive acrosomal remnants were observed within pleomorphic structures resembling fragments of sperm heads containing nuclear material (FIG. 15I). Examples were also observed (FIGS. 15J–K) of a peripheral cuff of MHS-10 positive reaction product beneath the limiting membrane of the cell.

Figure 15L:
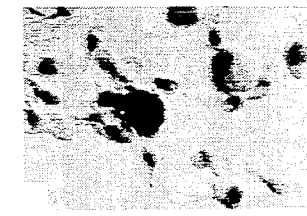
FIG. 15L. Leukocyte in semen smear stained with anti-HLe-1. Note lack of immunohistostaining of spermatids and mature sperm in the same field, (anti HL3-1, SBP, hematoxylin x845).

In the negative control experiments in which PBS was used instead of the mAb in semen smears, there was no red-brown immunoreaction product due to immunoperoxidase and only the blue hematoxylin counterstain of sperm and round cells was observed (data not shown). In semen smears that had been treated with the anti- HIe-1 monoclonal antibody, only the leukocytes reacted histochemically, as evidenced by the red-brown stain of AEC. Mature sperm and spermatids did not cross react with the anti-HLe1 antibody and remained blue (FIG. 15L).

Discussion

At present, it is difficult during semen analysis to distinguish leukocytes from sperm precursors using conventional light microscopic methods. The general category of "round cells" often serves to distinguish all other cell types present in semen from sperm. The conventional staining techniques used in the past such as the Papanicolaou stain or a combination of Leishman's blood stain and Bryan's sperm stain impart only general morphological information on the cellular components of the ejaculates. Overlap in sizes of the "round cells" is one cause of difficulties in definitive diagnosis. Granular leukocytes range in size from 9–14 mm while nongranular leukocytes range from 6–12 $\mu$m. The average size of a spermatid is 5–6 $\mu$m in diameter. Analysis of semen smears containing mixtures of germ cells and leukocytes using conventional stains is time-consuming and requires careful inspection of individual round cells, with distinction between the lymphocyte and immature germ cells being particularly problematic.

In the present study, we made use of a unique monoclonal antibody and a standard immunoperoxidase technique employing the chromogen AEC to easily visualize the target round cells. The MHS-10 antibody in conjunction with this method localized sperm precursors beginning with the Golgi and subsequent phases of spermiogensis. Cryosections of human testis stained using this mAb have shown it to target a developmental stage-specific antigen, (SP-10), appearing on adluminal germ cells and mature sperm but not on spermatogonia. The intra-acrosomal locus of the SP-10 antigen as well as its testis specificity have been established. The antigen is absent on cells from adrenals, colon, brain, skin, tonsils, lungs, liver, kidney, ovary, and endometrium and does not react with serum and peripheral blood leukocytes. Conversely, the leukocyte antibody HLe-1, as was confirmed in the present study, does not react with germ cells or mature sperm.

The application of the MHS-10 mAb probe to semen smears allows the detection of sperm as well as immature germ cells that had been previously sloughed off from the testis at various stages of spermiogenesis. Jassim and Festenstein, op. cit., have used a mouse anti-human sperm polyclonal antibody to visualize round cells in semen. Immunological identification of the various stages of germ cell differentiation, however, was not possible at the light microscopy level in their study, since the antibody used was not acrosome-specific and reacted with the cell surface of all germ cells. Their studies at the electron microscopy level, however, showed the presence of germ cells at various stages of differentiation. These authors have also demonstrated the presence of germ cells with abnormal morphology (such as binucleated cells) in semen. Electron microscopy was the method of choice by which this could be demonstrated. The latter method, although affording high resolution morphological data, is time-consuming and would have little application in clinical laboratory settings. The MHS-10 monoclonal antibody immunoreagent offers advantages of constant affinity and class, uniformity and availability in virtually unlimited supply, giving diagnosis of the MHS-10 positive subset of spermatids a standard of uniformity and reproducibility that was previously difficult to achieve with polyclonal immunoreagents.

Immunohistochemical staining of semen smears using MHS-10 allowed the identification of clusters of daughter spermatids connected by intracellular bridges. Such clusters could be indicative of failure of cytokinesis. Partial failures of the testis in the disjunction process may account for the presence of multinucleated sperm in the ejaculate. When groups of germ cells connected by intracellular bridges are not subjected to added disruptive forces in the testis, the constrictions between them gradually disappear and a spherical multinucleated mass is formed that contains as many nuclei as were conjoined in the original cluster of cells. Although the exact stage and mechanism(s) of the separation of spermatids into individual spermatozoa is not known, the MHS-10 probe allows for rigid quantitation of such cell associations.

Spermatids found joined together by intracellular bridges are more likely to occur in a syncytial relationship, and in normal spermatogenesis, coordination of development is achieved by uniform distribution of chemical factors controlling differentiation. Thus, it is not clear why cohorts of coupled spermatids stained with MHS-10 were observed to be at different stages of acrosome formation (FIGS. 15D-E). Dym and Fawcett, Biol. Reprod., 4:195 (1971), incorporated herein by reference, reported the occurrence of multiple transverse cisternae in the bridges joining dividing spermatogonia of the ram and rat. The presence of these membranous structures temporarily interrupted the continuity between the cell bodies of the conjoined cells, thus resulting in slight asynchrony of their cellular development. The membrane-limited cisternae persisted for only a short time after reconstitution of the nuclei of the daughter cells, although septate bridges were also observed in association with postkaryokinetic spermatid nuclei. Observations such as these have been limited to testis of experimental animals and have never been reported in human semen. The MHS-10 antibody probe has thus allowed documentation of the occurrence of asynchromous cohorts of spermatids in human semen for the first time.

Our understanding of all the factors controlling cytokinesis in the testis and the mechanism by which germ cells, either in clusters, or individually, are shed (spermiation) into the ejaculate is poorly understood. Further studies on the significance of germ cells in semen need to be undertaken. The MHS-10 probe may prove very useful in defining the relative proportion of specific subsets of germ cells prematurely shed at specific stages of their development, a categorization which could help clarify different types of testicular pathology underlying the cause of "round cell"syndrome. Soderstrom and Suominen, *Arch. Pathol. Lab. Med.*, 104:476 (1980), incorporated herein by reference, have demonstrated by electron microscopy studies on testicular biopsies that meiotic arrest is associated with an accumulation of pachytene spermatocytes and a lack of spermatids in the seminiferous tubules. This increase would be likely to be reflected in the semen of such patients such that the use of a stage-specific mAb reacting with pachytene spermatocytes would be a useful marker for the rapid identification of patients with meiotic arrest. In the same way, cellular accumulation in semen of a specific stage of spermatid development identified by MHS-10 could shed light upon a pathology causing subfertility or infertility of men with "round cell" syndrome.

In summary, acetone dried smears from washed human semen containing significant numbers of round cells were probed with mAb MHS-10. Monoclonal antibody labelled cells were visualized by a standard streptavidin-biotin immunoperoxidase method using a light microscope. The MHS-10 mAb immunoreacted with mature sperm and with a subset of round cells diagnosed as developing spermatids which has been sloughed off from the testis at varying stages of acrosome formation. To rule out possible cross-reactivity of the mAb with leukocytes in semen, a leukocyte surface marker (anti- HLe-1) was used in conjunction with MHS-10. Round cell populations staining with MHS-10 did not stain with anti-HLe-1. The MHS-10 mAb provides a unique immunoreagent for differential diagnosis of a subset of immature germ cells during semen analysis. The mAb MHS-10 is thus a promising probe for the identification and quantitation of immature germ cells in human semen.

Summary of Experimental Results

The above examples show that the human sperm protein, SP10, is a differentiation antigen which is detected in round spermatids at the Golgi phase and subsequent steps of spermiogenesis. SP-10 localizes within the nacent acrosomal vesicle of spermatids, is an intra-acrosomal protein in mature sperm, and appears to be testis-specific. The protein remains associated with the equatorial segment and/or inner acrosomal membranes of ionophore induced acrosome reacted sperm.

These observations have led to the suggestion that SP-10 and its cognate monoclonal antibody MHS-10 provide a useful marker/probe system for: a) diagnosing immature germ cells in semen; and b) scoring the acrosome reaction. Furthermore, SP-10 has been designated a "primary vaccine candidate" by the World Health Organization Taskforce on Contraceptive Vaccines, due to its tissue specificity and evidence that the MHS-10 monoclonal antibody inhibits fertilization in the hamster egg penetration test.

On immunoblots of human sperm extracts, polymorphism of immunoreactive SP-10 peptides are observed to range from 18 to 34 kDa. This pattern of immunoreactivity with the monoclonal antibody MHS-10 has been shown to be conserved from individual to individual and to be unaffected by reducing agents. Western blots of 2-D gels have shown that the antigenic peptides of 24–34 kD have a pI of 4.9 whereas the peptides of approximately 18 kD are more basic, with pI's ranging from 5.1–5.4.

cDNAs coding for the intra-acrosomal protein SP-10 were cloned and characterized. Three overlapping SP-10 specific cDNAs were isolated from a human testis cDNA expression library. These cDNAs hybridized to a 1.35kb mRNA which was present in human testes but was not found in liver or placenta. Complete sequencing of these cDNAs produced an 1117 bp sequence containing a 265 amino acid coding region for the SP-10 protein. SP-10 has a predicted molecular weight of 28.3 kD. Hydrophobicity plots generated from the deduced amino acid sequence showed a very hydrophobic amino terminus characteristic of a signal peptide. SP-10 appears to be a unique acrosomal protein based on previous immunohistological data and on the observation that SP-10 cDNA sequences did not show any significant homology to other sequences found in three databases.

A recombinant SP-10 fusion protein was produced in an *E. coli* expression vector and this prototype recombinant vaccine was used to generate a polyclonal antisera in rabbits. This rabbit antisera stained the acrosomal cap in-situ and reacted with a similar set of peptides on Western blots as did a monoclonal antibody to SP-10. The rabbits did not appear to suffer from the vaccine. These results show that a recombinant SP-10 vaccine is capable of evoking in mammals an immune response which recognizes the native human sperm SP-10.

It will be apparent to those skilled in the art that various modifications and variations can be made to the products and processes of the present invention. Thus, it is intended that the present invention covers such modifications and variations, provided they come within the scope of the appended claims and their equivalents.

TABLE I

Segregation of DNA Probe SP-10 with Human Chromosomes in EcoRI digested Human-Mouse Cell Hybrid DNA

| HYBRID | DNA# | SP-10 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Translocations |
|---|---|---|---|---|---|---|---|---|---|---|---|---|---|---|---|---|---|---|---|---|---|---|---|---|---|---|
| ATR-13 | 48 | − | + | + | + | + | + | + | + | + | − | − | − | − | + | + | + | + | + | + | + | − | − | − | ± | 5/X |
| DUA-3BSAGA | 233 | − | − | + | + | − | − | − | + | + | − | − | + | − | + | + | − | − | + | − | + | − | + | − | − | |
| DUA-5BSAGA | 197 | + | − | − | − | − | − | − | − | − | − | − | − | − | − | − | + | − | − | − | − | − | − | − | − | |
| DUA-6 | 859 | + | + | + | + | − | + | + | + | − | − | + | − | + | + | + | + | − | − | + | + | + | + | + | + | |
| DUM-13 | 186 | + | − | − | + | − | + | + | + | − | − | + | + | + | − | + | ± | + | + | + | + | + | + | + | ± | X/15, 15/X |
| JSR-2 | 389 | − | − | − | + | − | + | + | + | − | − | + | + | + | − | + | − | − | + | + | − | + | + | − | − | |
| JSR-14 | 402 | + | + | + | + | + | + | + | − | − | − | + | + | + | − | + | − | + | + | − | − | + | + | + | − | |
| JSR-17S | 44 | + | ± | + | − | + | + | − | ± | − | − | + | + | + | + | + | + | − | + | − | − | + | + | − | + | 7/9 |
| JWR-22H | 653 | + | ± | ± | + | + | + | + | ± | − | − | + | + | + | + | + | + | − | + | − | − | + | + | + | − | 2/1 |
| JWR-26C | 187 | − | − | − | − | − | + | + | + | + | − | + | + | + | − | + | + | + | + | + | − | − | + | + | + | 1/2 |
| NSL-16 | 192 | − | − | + | + | + | + | + | + | + | ± | + | − | + | + | + | + | + | + | + | − | − | − | − | + | 17/9 |
| REW-11 | 42 | + | + | − | − | − | − | − | − | − | − | − | + | − | − | − | − | − | − | − | − | − | − | − | − | |
| REX-11BSAgB | 184 | − | − | + | − | − | − | − | + | + | − | + | + | + | + | + | − | − | + | − | + | − | + | + | + | |
| REX-11BSHF | 254 | − | − | − | + | − | − | − | + | + | − | + | + | + | − | − | − | − | − | − | − | − | + | − | − | 22/X |
| RSR-3 | 1162 | + | + | + | + | + | + | + | + | + | + | + | + | + | + | + | + | + | + | + | + | + | + | + | + | |
| SIR-8 | 673 | + | − | − | − | − | − | − | + | − | − | − | − | − | − | − | − | − | − | − | − | − | − | − | − | |
| SIR-11 | 390 | + | − | − | + | + | + | + | + | + | + | + | + | + | + | + | + | + | + | + | + | + | + | + | + | |
| TSL-1 | 643 | − | − | − | − | − | − | − | − | − | − | + | − | + | − | + | − | − | ± | + | + | + | − | − | + | |
| TSL-2 | 644 | − | − | − | + | − | − | − | − | + | − | + | + | + | + | + | − | − | + | + | + | + | − | − | + | 17/3 |
| VTL-6 | 395 | + | − | + | + | + | + | + | + | + | + | + | + | + | + | + | + | − | + | + | + | + | + | + | + | |
| WIL-1 | 20 | + | − | + | + | + | + | + | + | + | + | + | ± | + | + | + | + | + | + | + | + | + | + | + | + | |
| WIL-2 | 12 | − | − | + | + | + | + | + | + | + | + | + | ± | + | + | + | + | + | + | + | + | + | + | + | + | |
| WIL-5 | 9 | + | − | − | − | − | − | − | − | − | − | − | + | − | − | − | − | − | − | − | − | − | − | − | − | |
| WIL-7 | 13 | + | − | + | + | + | + | + | + | + | + | + | ± | + | + | + | + | + | + | + | + | + | + | + | + | |
| WIL-14 | 347 | − | + | + | + | + | + | + | + | + | + | + | + | + | + | + | + | + | + | + | + | + | + | + | + | |
| WIL-15 | 25 | + | + | + | + | + | + | + | + | + | + | + | + | + | + | + | + | + | + | + | + | + | + | + | + | |
| W12 | 559 | + | − | − | − | − | − | − | − | − | − | − | + | − | − | − | − | − | − | − | − | − | − | − | − | 11p- |
| XOL-6 | 534 | − | ± | − | + | − | + | + | + | − | − | − | + | − | + | + | + | − | − | + | + | + | − | − | ± | 1/X |
| XOL-9 | 554 | + | ± | − | − | − | − | − | − | − | − | − | + | − | − | − | − | − | − | − | − | − | − | − | ± | X/1 |
| XOL-21 | 1107 | − | − | − | + | − | − | − | − | − | − | − | + | + | + | + | + | + | + | + | + | + | + | + | + | ISO7p |
| XTR-3BSAgB | 57 | + | + | + | + | + | + | + | + | + | + | + | + | + | + | + | + | + | + | + | + | + | + | + | ± | 3/X, 10q- |
| EXR-5CSAz | 64 | − | + | − | − | − | − | − | − | − | − | − | + | − | − | − | − | − | − | − | − | − | − | − | + | X/11 |
| EXR-5CSAZ | 952 | ± | + | + | + | + | + | + | + | + | + | + | − | + | + | + | + | + | + | + | + | + | + | + | + | X/11 |
| XER-7 | 640 | + | + | + | + | + | + | + | + | + | + | + | − | + | + | + | + | + | + | + | + | + | + | + | + | 11/X |
| XER-7 | 961 | + | + | + | + | + | + | + | + | + | + | + | − | + | + | + | + | + | + | + | + | + | + | + | + | 11/X |
| Chromosome | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | |
| Concordant # of Hybrids | | | 18 | 21 | 18 | 18 | 20 | 21 | 20 | 16 | 21 | 22 | 31 | 18 | 20 | 21 | 16 | 23 | 20 | 18 | 19 | 20 | 21 | 20 | 12 | |
| Discordant # of Hybrids | | | 13 | 13 | 15 | 17 | 15 | 14 | 13 | 19 | 13 | 12 | 0 | 17 | 15 | 14 | 18 | 12 | 14 | 16 | 15 | 12 | 14 | 14 | 18 | |
| *Discordancy | | | 42 | 38 | 45 | 49 | 43 | 40 | 39 | 54 | 38 | 35 | 0 | 49 | 43 | 40 | 53 | 34 | 41 | 46 | 43 | 34 | 40 | 41 | 60 | |

We claim:

1. Isolated DNA which encodes a polypeptide having the amino acid sequence 1–265 of FIGS. 11A and 11B.

2. Isolated DNA which encodes an intra-acrosomal human sperm antigen that remains with said human sperm after said sperm has undergone an acrosome reaction, said antigen having a molecular weight of 18–34 kilodaltons and an isoelectric 4.9–5.4, wherein said DNA has the nucleotide sequence 61–855 of FIGS. 11A and 11B.

3. An expression vector for the transformation of an expression host, comprising heterologous DNA which comprises DNA which encodes an intra-acrosomal sperm antigen that remains with said human sperm after said sperm has undergone an acrosome reaction, said antigen having the molecular weight of 19÷kilodaltons and an isoelectric point at 4.9–5.4, wherein said antigen has the amino acid sequence 1–265 of FIGS. 11A and 11B, operably linked to a regulatory control DNA.

4. An expression vehicle for the expression of an intra-acrosomal human sperm antigen that remains with said human sperm after said sperm undergoes an acrosome reaction, comprising an *E. coli* with DNA comprising the expression vector of claim 3.

* * * * *